(12) United States Patent
Tryggvason et al.

(10) Patent No.: US 12,221,624 B2
(45) Date of Patent: Feb. 11, 2025

(54) SYSTEMS AND METHODS FOR PRODUCING RETINAL PROGENITORS

(71) Applicant: National University of Singapore, Singapore (SG)

(72) Inventors: Karl Tryggvason, Singapore (SG); Hwee Goon Tay, Singapore (SG); Aida Moreno Moral, Singapore (SG)

(73) Assignee: National University of Singapore, Singapore (SG)

( * ) Notice: Subject to any disclaimer, the term of this patent is extended or adjusted under 35 U.S.C. 154(b) by 763 days.

(21) Appl. No.: 16/755,312

(22) PCT Filed: Oct. 17, 2018

(86) PCT No.: PCT/SG2018/050517
§ 371 (c)(1),
(2) Date: Apr. 10, 2020

(87) PCT Pub. No.: WO2019/078783
PCT Pub. Date: Apr. 25, 2019

(65) Prior Publication Data
US 2021/0189328 A1  Jun. 24, 2021

Related U.S. Application Data

(63) Continuation-in-part of application No. PCT/SG2017/050520, filed on Oct. 17, 2017.

(51) Int. Cl.
*C12N 5/0793* (2010.01)
*C12P 21/02* (2006.01)

(52) U.S. Cl.
CPC .............. *C12N 5/062* (2013.01); *C12P 21/02* (2013.01); *C12N 2500/98* (2013.01); *C12N 2501/13* (2013.01); *C12N 2501/15* (2013.01); *C12N 2501/415* (2013.01); *C12N 2501/999* (2013.01); *C12N 2506/45* (2013.01); *C12N 2533/52* (2013.01)

(58) Field of Classification Search
None
See application file for complete search history.

(56) References Cited

U.S. PATENT DOCUMENTS

| | | | |
|---|---|---|---|
| 6,693,169 | B1 | 2/2004 | Brunken et al. |
| 2015/0299653 | A1 | 10/2015 | Hovatta et al. |
| 2016/0175362 | A1 | 6/2016 | Lanza et al. |
| 2016/0244721 | A1 | 8/2016 | Sawada et al. |

FOREIGN PATENT DOCUMENTS

| | | | |
|---|---|---|---|
| CA | 3021828 A1 | | 10/2017 |
| CN | 107148276 A | | 9/2017 |
| WO | WO 2013/184809 A1 | | 12/2013 |
| WO | 2014145108 A1 | | 9/2014 |
| WO | 2017021972 A1 | | 2/2017 |
| WO | WO 2017/091844 A1 | | 6/2017 |
| WO | 2018146679 A2 | | 8/2018 |

OTHER PUBLICATIONS

Retinal precursor cells—Wikipedia (downloaded from < Retinal precursor cells—Wikipedia >, on Mar. 25, 2023, pp. 1-2).*
Zhong et al (Nat Comm 5: 1-14, 2014).*
Sridhar et al (Stem Cells Translat Med 5: 417-426, 2016).*
Synergistic effect definition:<synergistic effect definition—Search (bing.com)—Search>, downloaded Nov. 4, 2023, one page (Year: 2023).*
Kaewkhaw, Rossukon et al., Transcriptome Dynamics of Developing Photoreceptors in Three-Dimensional Retina Cultures Recapitulates Temporal Sequence of Human Cone and Rod Differentiation Revealing Cell Surface Markers and Gene Networks, Stem Cells, 2015, 33:3504-3518, Translational and Clinical Research.
MacDonald P R et al: "Laminin chain assembly is regulated by specific coiled-coil interactions", Journal of Structural Biology, Academic Press, United States, vol. 170, No. 2, May 1, 2010 (May 1, 2010), pp. 398-405, XP0270337040, ISSN: 1047-8477 [retrieved on Feb. 13, 2010] * p. 401, left-hand column; table 2 *.
Deepak A Lamba et al: "Efficient generation of retinal progenitor cells from human embryonic stem cells", Proceedings National Academy of Sciences, National Academy of Sciences, US. vol. 103, No. 34, Aug. 22, 2006 (Aug. 22, 2006), pp. 12759-12774, XP008155440, ISSN: 0027-8424, DOI: 10.1073/PNAS.0501990103 [retrieved on Aug. 14, 2006] *material and methods; figure 2*.
Gong J et al: "Effects of extracellular matrix and neighboring cells on induction of human embryonic stem cells into retinal or retinal pigment epithelial progenitors". Experimental Eye Research, Academic Press Ltd, London, vol. 86, No. 6,Jun. 1, 2008 (Jun. 1, 2008), pp. 957-965, XP022709066, ISSN: 0014-4835, DoI: 10.1016/J. EXER.2008.03.014 [retrieved on Mar. 28, 2008] *abstract*.
Anna Domogatskaya et al: Functional Diversity of Laminins, Annual Review of Cell and Developemental Biology., vol. 28, No. 1 Nov. 10, 2012 (Nov. 10, 2012), pp. 523-553, XP055222350, US ISSN: 1081-0706, DO1: 10.1146/annurev-cellbio-101011-155750 *the whole document *.
Partial Supplementary European Search Report for European Patent Application No. 18867391.7 dated Jul. 14, 2021.
Barnea-Cramer A. 0. et al., Function of human pluripotent stem cell-derived photoreceptor progenitors in blind mice. Sci. Rep., Jul. 13, 2016, vol. 6, No. 2016, pp. 29784: 1-15.

(Continued)

*Primary Examiner* — Kimberly Ballard
*Assistant Examiner* — Aditi Dutt
(74) *Attorney, Agent, or Firm* — Lippes Mathias LLP

(57) ABSTRACT

Retinal progenitors and mature photoreceptor cells can be produced by differentiating human embryonic stem cells on a surface having a laminin matrix thereon made of two laminins One laminin is laminin-521, and the other laminin is either laminin-323 or laminin-523. Stem cells plated on this substrate can be differentiated using various cell culture mediums to obtain the retinal progenitors and mature photoreceptor cells.

15 Claims, 25 Drawing Sheets

(56) References Cited

OTHER PUBLICATIONS

Kanninen L. K. et al., Laminin-511 and laminin-521-based matrices for efficient hepatic specification of human pluripotent stem cells. Biomat., Jun. 23, 2016, vol. 103, No. 2016, pp. 86-100.
Laminin. Jul. 31, 2017 [Retrieved on Dec. 31, 2018 from https://web.archive.org/web/20170731163828/https://en.wikipedia.org/wiki/Laminin; for the purpose of internet archive to establish publication date] "Types" section.
Libby R. T. et al., Laminin expression in adult and developing retinae: evidence of two novel CNS laminins. J Neurosci., Sep. 1, 2000, vol. 20, No. 17, pp. 6517-6528: 1-31.
Ohta R. et al., Laminin-guided highly efficient endothelial commitment from human pluripotent stem cells. Sci Rep, Nov. 2, 2016, vol. 6, No. 35680 (2016), pp. 1-12.
Schmitt S. et al, Molecular characterization of human retinal progenitor cells. Invest Ophthalmol Vis Sci, Jun. 24, 2009, vol. 50, No. 12, pp. 5901-5908.
Varshney S. et al., Laminin β2 and γ3 chains chains regulate proliferation and differentiation of retinal progenitor cells, *Investig. Opthalmol. Vis. Sci*, Jun. 30, 2013, vol. 54, No. 15, pp. 3745.
Birthe Dorgau, et al, "Laminin γ3 plays an important role in retinal lamination, photoreceptor organisation and ganglion cell differentiation" Cell Death & Disease, 2018 pp. 1-13.
Chinese Office Action of Application No. 201880081377.0 Dated Sep. 19, 2022.
Hwee Goon Tay et al., "Photoreceptor laminin drives differentiation of human pluripotent stem cells to photoreceptor progenitors that partially restore retina function", Molecular Therapy, Mar. 2023, p. 825-846, V 31 I 3, Plum X Metrics.
Rajiv Saigal et al., "Electrical Stimulation via a Biocompatible Conductive Polymer Directs Retinal Progenitor Cell Differentiation", Jul. 2013 35th Annual International Conference of the IEEE Engineering in Medicine and Biology Society (EMBC).
Catherine Jomary and Stephen Jones, "Induction of Functional Photoreceptor Phenotype by Exogenous Crx Expression in Mouse Retinal Stem Calls", Investigative Ophthalmology & Visual Science, Jan. 2008, 429-437, V 49 N1, Association for Research in Vision and Ophthalmology.
Singapore Office Action for Application No. 1120203534Y Dated: Aug. 12, 2024.

* cited by examiner

LC-MS/MS results of LN523 clone 1

| Accession | Description | Score | Coverage | # Proteins | # Unique Peptides | # Peptides | # PSMs | Area | # AAs | MW [kDa] | calc. pI |
|---|---|---|---|---|---|---|---|---|---|---|---|
| O15230 | Laminin subunit alpha-5 OS=Homo sapiens GN=LAMA5 PE=1 SV=8 - [LAMA5_HUMAN] | 663.89 | 6.25% | 1 | 18 | 18 | 20 | 7.94E+07 | 3695 | 399.5 | 7.02 |
| P55268 | Laminin subunit beta-2 OS=Homo sapiens GN=LAMB2 PE=1 SV=2 - [LAMB2_HUMAN] | 1352.19 | 33.26% | 1 | 36 | 36 | 47 | 2.57E+08 | 1798 | 195.9 | 6.52 |
| Q9Y6N6 | Laminin subunit gamma-3 OS=Homo sapiens GN=LAMC3 PE=1 SV=3 - [LAMC3_HUMAN] | 27.82 | 2.22% | 1 | 1 | 2 | 2 | 2.39E+07 | 1575 | 171.1 | 6.58 |

FIG. 1D

LC-MS/MS results of LN323 clone 14

| Accession | Description | Score | Coverage | # Proteins | # Unique Peptides | # Peptides | # PSMs | Area | # AAs | MW [kDa] | calc. pI |
|---|---|---|---|---|---|---|---|---|---|---|---|
| Q16787 | Laminin subunit alpha-3 OS=Homo sapiens GN=LAMA3 PE=1 SV=2 - [LAMA3_HUMAN] | 794.34 | 16.77% | 1 | 39 | 39 | 43 | 3.58E+08 | 3333 | 366.4 | 7.24 |
| P55268 | Laminin subunit beta-2 OS=Homo sapiens GN=LAMB2 PE=1 SV=2 - [LAMB2_HUMAN] | 1238.86 | 38.21% | 2 | 50 | 50 | 67 | 1.74E+09 | 1798 | 195.9 | 6.52 |
| Q9Y6N6 | Laminin subunit gamma-3 OS=Homo sapiens GN=LAMC3 PE=1 SV=3 - [LAMC3_HUMAN] | 90.27 | 5.33% | 1 | 4 | 6 | 7 | 1.73E+08 | 1575 | 171.1 | 6.58 |

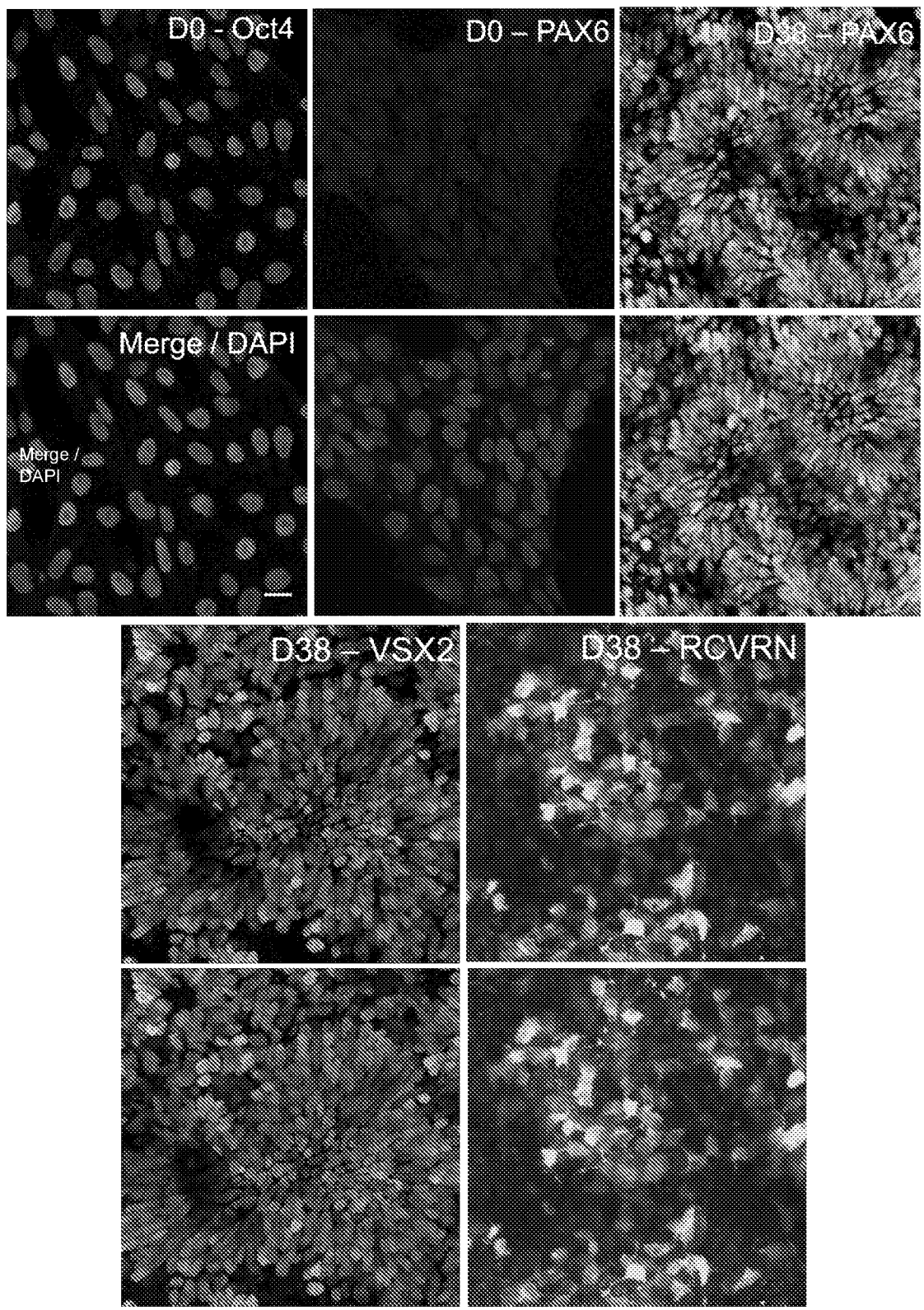
LN-523 + LN-521   FIG. 3A

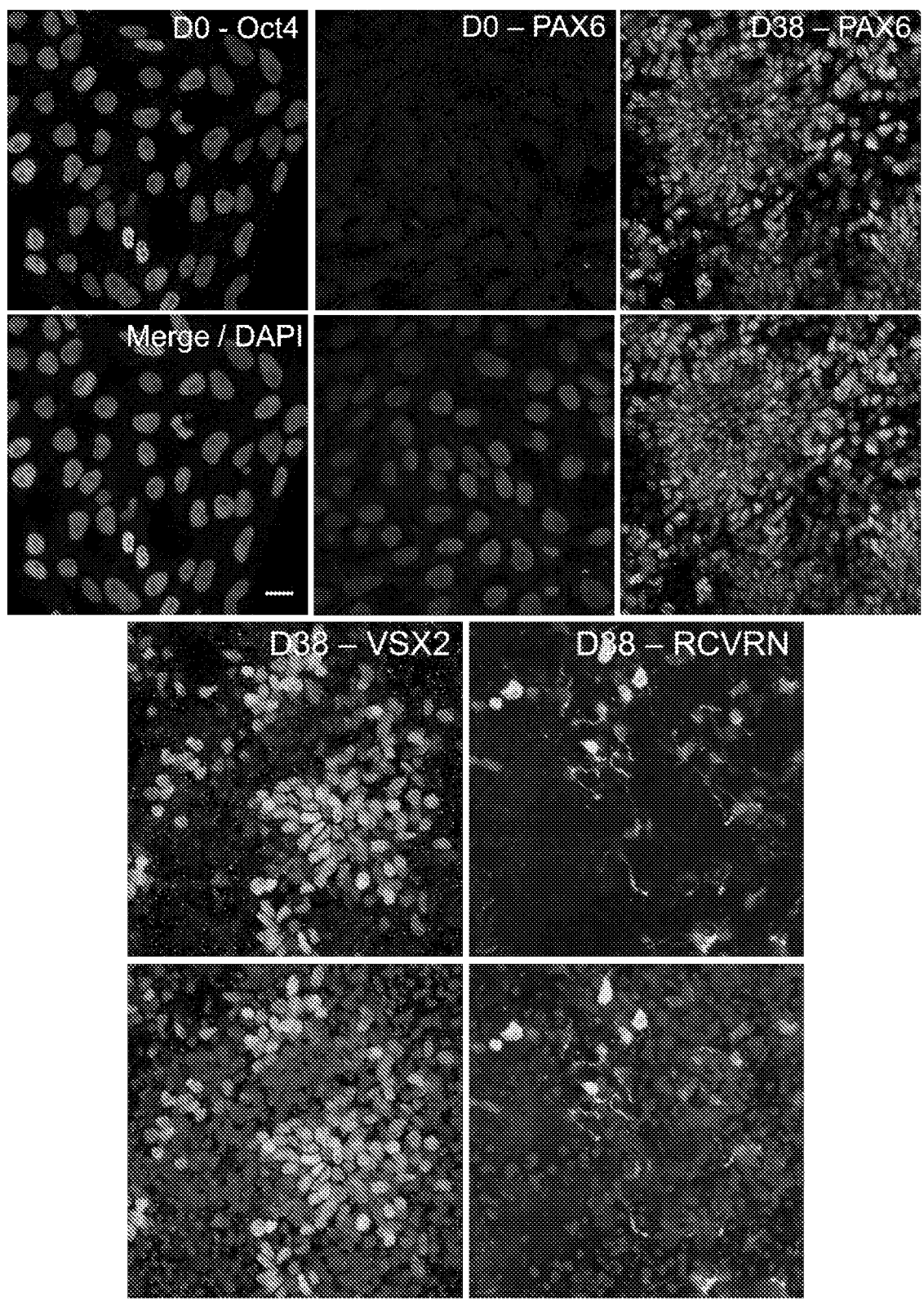
LN-323 + LN-521    FIG. 3B

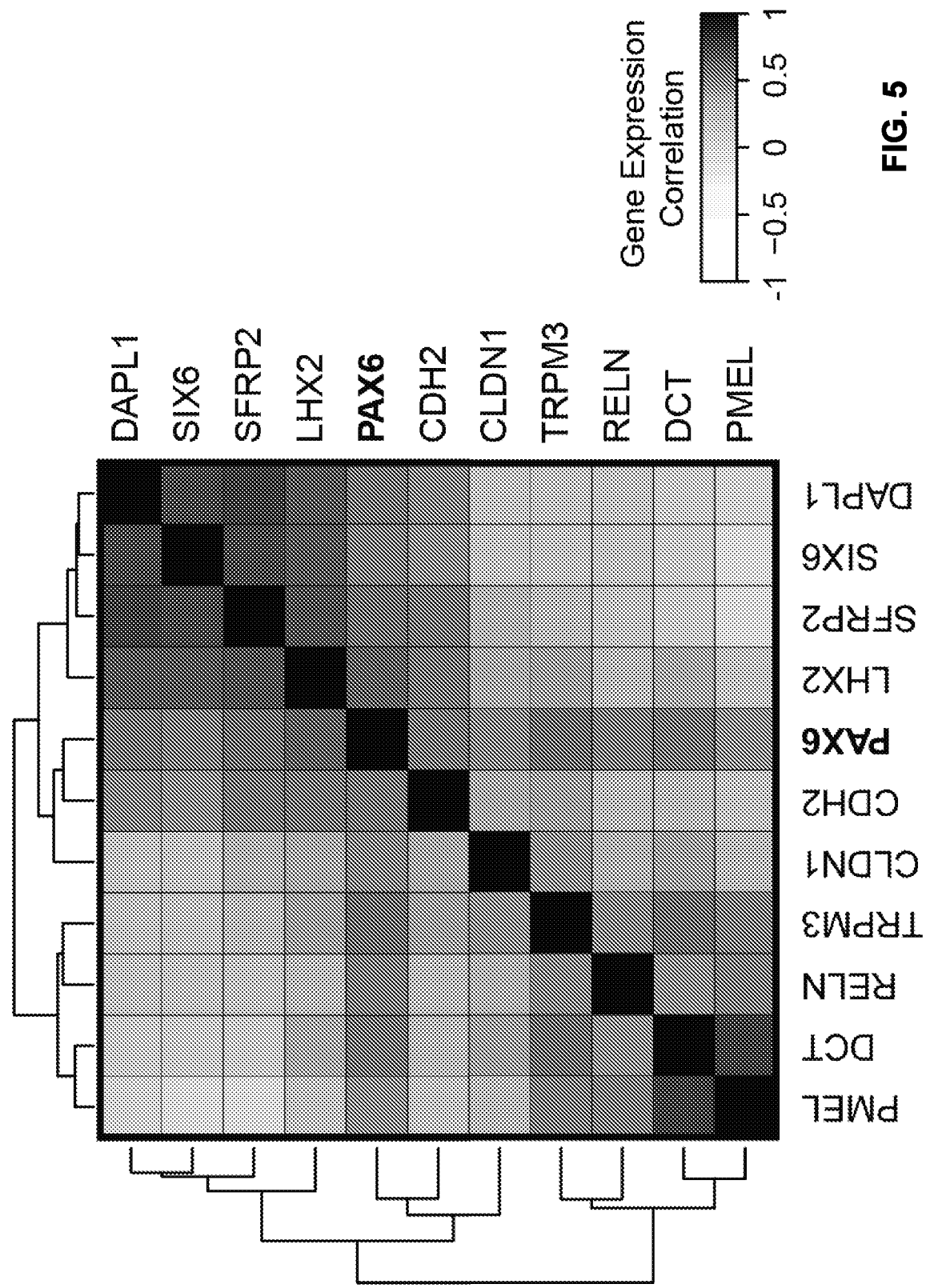

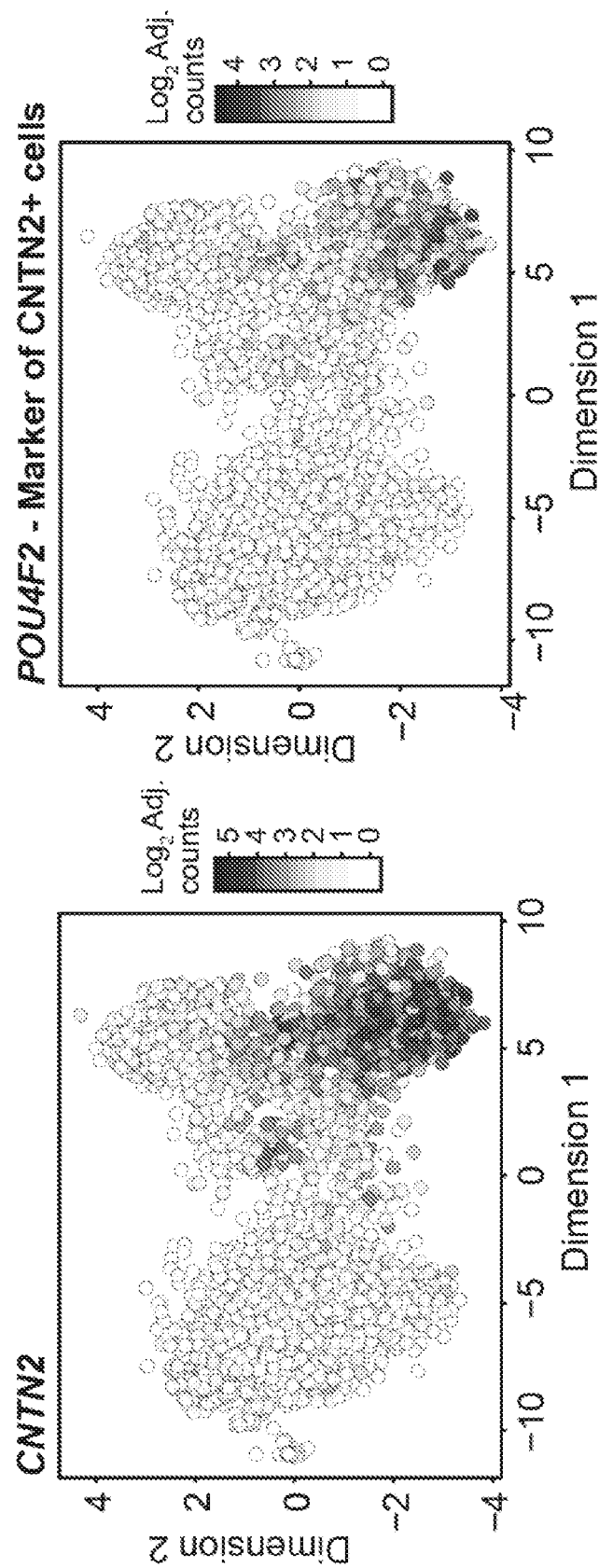

SYSTEMS AND METHODS FOR PRODUCING RETINAL PROGENITORS

CROSS-REFERENCE TO RELATED APPLICATIONS

This application is a 371 of PCT Application No. PCT/SG2018/050517 filed Oct. 17, 2018, which claims priority to PCT Application No. PCT/SG2017/050520, filed Oct. 17, 2017, which are fully incorporated by reference.

BACKGROUND

The present disclosure relates to systems and methods for producing retinal progenitor cells (such as photoreceptor progenitor cells or ganglion progenitor cells) or retinal photoreceptor cells from human pluripotent stem cells. Compositions and matrices for use in such systems and methods are also disclosed. Transplantation of the resulting retinal progenitor cells or retinal photoreceptor cells is further disclosed and included herein. These methods, compositions, and systems comprising the same are useful for treating eye conditions such as macular degeneration (MD) or retinitis pigmentosa (RP).

The chief causes of blindness worldwide are Age-related Macular Degeneration (AMD) and Retinitis Pigmentosa (RP). These two conditions involve the loss of photoreceptors and the underlying retina pigmented epithelium (RPE). Functional interplay between the photoreceptors and the RPE is required to support the visual system. Unfortunately, the human retina lacks the ability to regenerate when cells are lost to disease or injury, and no effective treatment exists to reverse retinal degeneration.

Post-mitotic human photoreceptors are not considered an ethical and suitable source for human cell replacement because they are only available after 19 weeks of pregnancy. Existing protocols for photoreceptors derived from stem cells are based on spontaneous differentiation of embryoid bodies in chemically un-defined culture conditions, mainly with the use of Matrigel® to form 3D optic cups or retinal organoids. These 3D organoids are not transplantation competent, and such protocols lead to heterogeneous retinal cell types with varied developmental stages.

In addition, Matrigel™ is a murine tumor extract containing several basement membrane proteins (e.g. type IV collagen, perlecan, laminin-111) as well as growth factors and intracellular proteins. Matrigel™ is thus xenogenic, affected by lot-to-lot variations, and contains an extensive amount of undefined components. Moreover, cells cultured on Matrigel™ also have the possibility of acquiring non-human N-glycolylneuraminic acid (Neu5Gc) immunogen which renders them unsuitable for clinical applications.

Current treatments include oral medications that include antioxidants (e.g. vitamin A palmitate), docosahexaenoic acid (DHA), calcium channel blockers, and lutein/zeaxanthin. However, none show effectiveness in restoring vision.

BRIEF DESCRIPTION

The present disclosure relates to systems and methods for obtaining retinal progenitor cells or retinal photoreceptor cells. Briefly, pluripotent stem cells are cultured on a substrate comprising a mixture of (i) laminin-323 (LN-323) or LN-523, and (ii) laminin-521. LN-323 and LN-523 have not previously been purified in pure form, and were produced for the first time as recombinant human proteins in human embryonic kidney cells (HEK-293), purified and as cell culture coatings. The stem cells are differentiated using two different cell culture mediums to obtain the retinal progenitor cells or retinal photoreceptor cells (depending on the length of time they are differentiated).

Five distinct subpopulations of retinal progenitor cells have also been identified. These five subpopulations can be identified by a Day 26-34 gene profile, as explained further herein.

In the first subpopulation (A), at least one of genes CRX, C11orf96, NXPH4, NTS, DCT, PRDM1, NEUROD4, S100A13, RCVRN, FAM57B, SYT4, DLL3, SSTR2, CHRNA5, and ROBO2 is expressed in the Day 26-34 gene profile. Desirably, more or most of these genes are expressed.

In the second subpopulation (B), at least one of genes STMN2, ONECUT2, ATOH7, ELAVL4, and GAP43 is expressed in the Day 26-34 gene profile. Desirably, more or most of these genes are expressed.

In the third subpopulation (C), at least one of genes CNTN2, NEFM, NEFL, PRPH, POU4F2, and CXCR4 is expressed in the Day 26-34 gene profile. Desirably, more or most of these genes are expressed.

In the fourth subpopulation (D), at least one of genes PAX6, SIX3, and SLC2A1 is expressed in the Day 26-34 gene profile. Desirably, more or most of these genes are expressed.

In the fifth subpopulation (E), at least one of genes VSX2, PTH2, FZD5, RARRES2, DIO3, SOX2, and CYP1B1 is expressed in the Day 26-34 gene profile. Desirably, more or most of these genes are expressed.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 1D is LC-MS/MS (Liquid Chromatography-Mass Spectrophotometry) results showing that LAMA5, LAMB2, and LAMC3 chains are present.

FIG. 1G is LC-MS/MS (Liquid Chromatography-Mass Spectrophotometry) results showing that LAMA3, LAMB2, and LAMC3 chains are present.

Figure 2A:
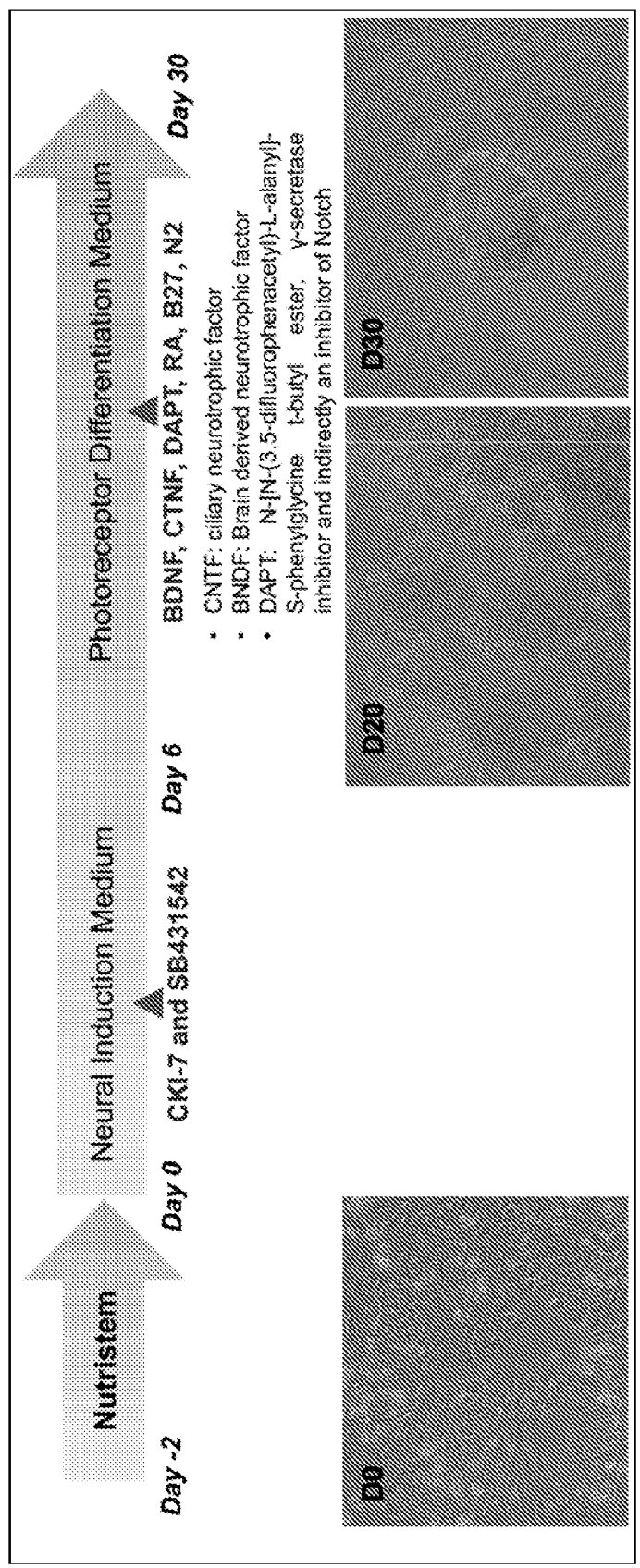
FIG. 2A is a diagram depicting a method of differentiating hESCs to photoreceptors. Three cell cultures are indicated: Nutristem for culturing prior to differentiation (Day 0); neural induction medium; and photoreceptor differentiation medium. Three pictures are also provided, showing the cells at D0, D20, and D30.
Figure 2B:
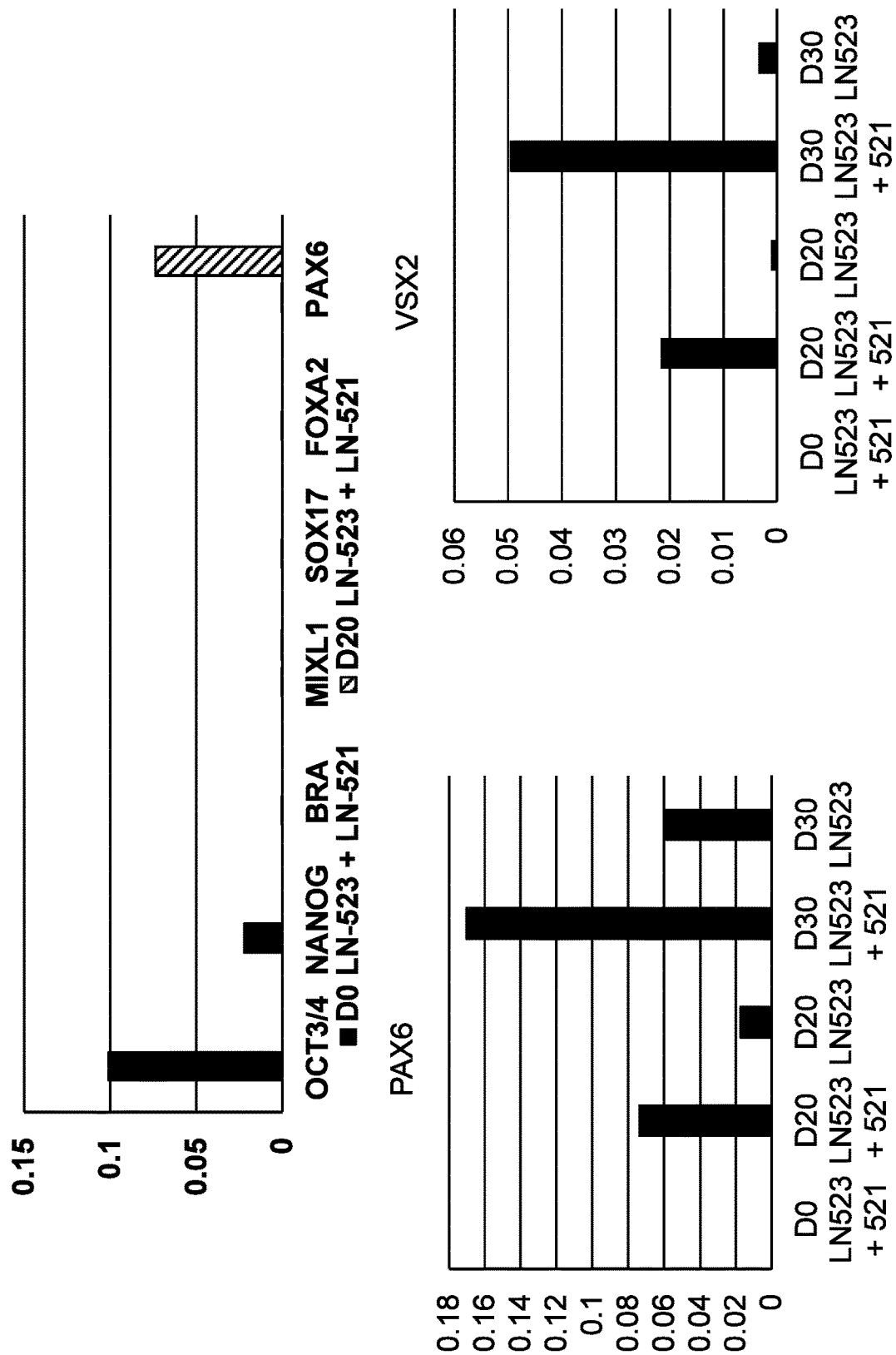
FIG. 2B and FIG. 2C are a set of five different graphs for the cells grown on the LN-523+LN-521 substrate. In the top graph of FIG. 2B, the y-axis is in arbitrary units, and runs from 0 to 0.15 in increments of 0.05. The x-axis is, from left to right, OCT3/4, NANOG, BRA, MIXL1, SOX17, FOXA2, and PAX6.

In the bottom left graph of FIG. 2B labeled PAX6, the y-axis is arbitrary units, and runs from 0 to 0.18 in increments of 0.02. The x-axis is, from left to right, D0 LN-523+LN-521, D20 LN-523+LN-521, D20 LN-523 only, D30 LN-523+LN-521, and D30 LN-523 only.

In the bottom right graph of FIG. 2B labeled VSX2, the y-axis is in arbitrary units, and runs from 0 to 0.06 in increments of 0.01. The x-axis is, from left to right, D0 LN-523+LN-521, D20 LN-523+LN-521, D20 LN523 only, D30 LN523+521, and D30 LN523 only.

Figure 2C:
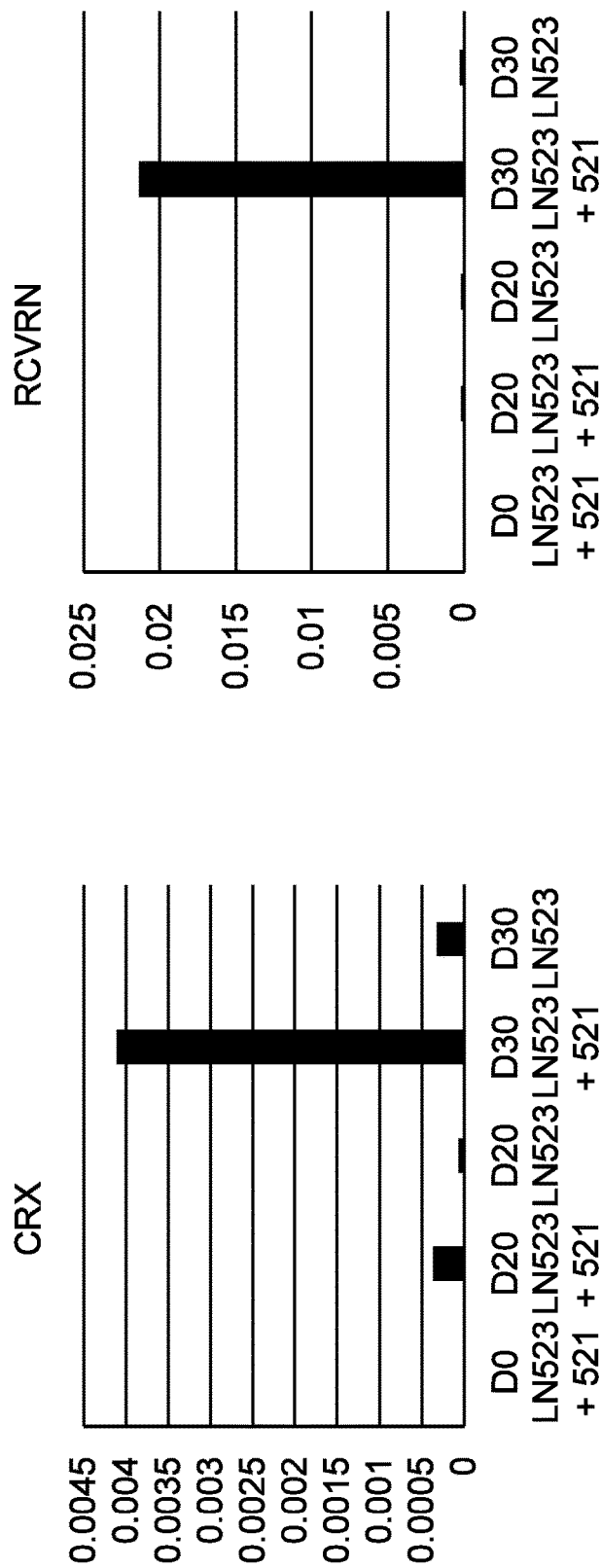

In the left graph of FIG. 2C labeled CRX, the y-axis is in arbitrary units, and runs from 0 to 0.0045 in increments of 0.0005. The x-axis is, from left to right, D0 LN523+521, D20 LN523+521, D20 LN523 only, D30 LN-523+LN-521, and D30 LN-523 only.

In the right graph of FIG. 2C labeled RCVRN, the y-axis is in arbitrary units, and runs from 0 to 0.025 in increments of 0.005. The x-axis is, from left to right, D0 LN-523+LN-521, D20 LN-523+LN-521, D20 LN-523 only, D30 LN-523+LN-521, and D30 LN-523 only.

Figure 2D:
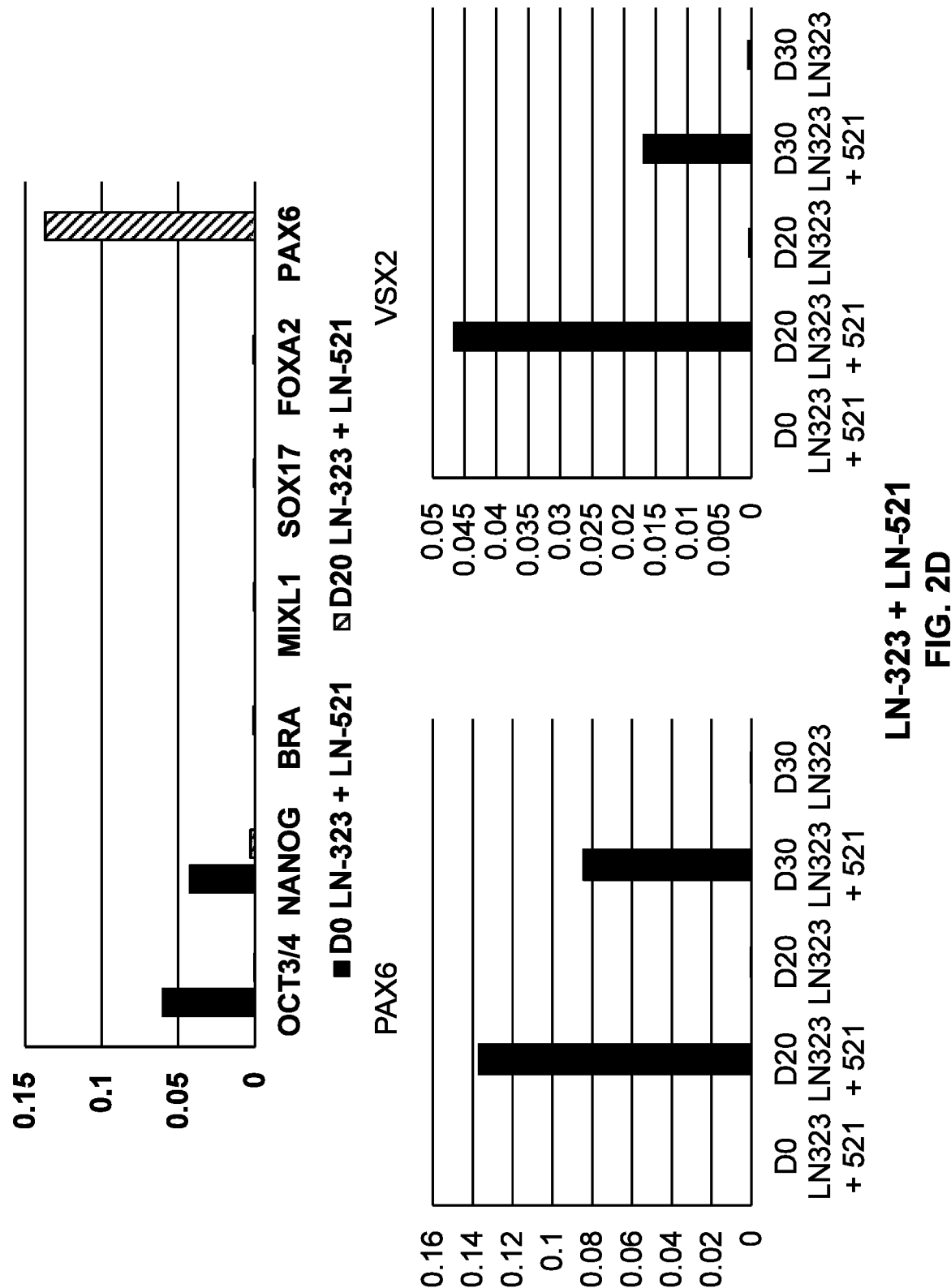
Figure 2E:
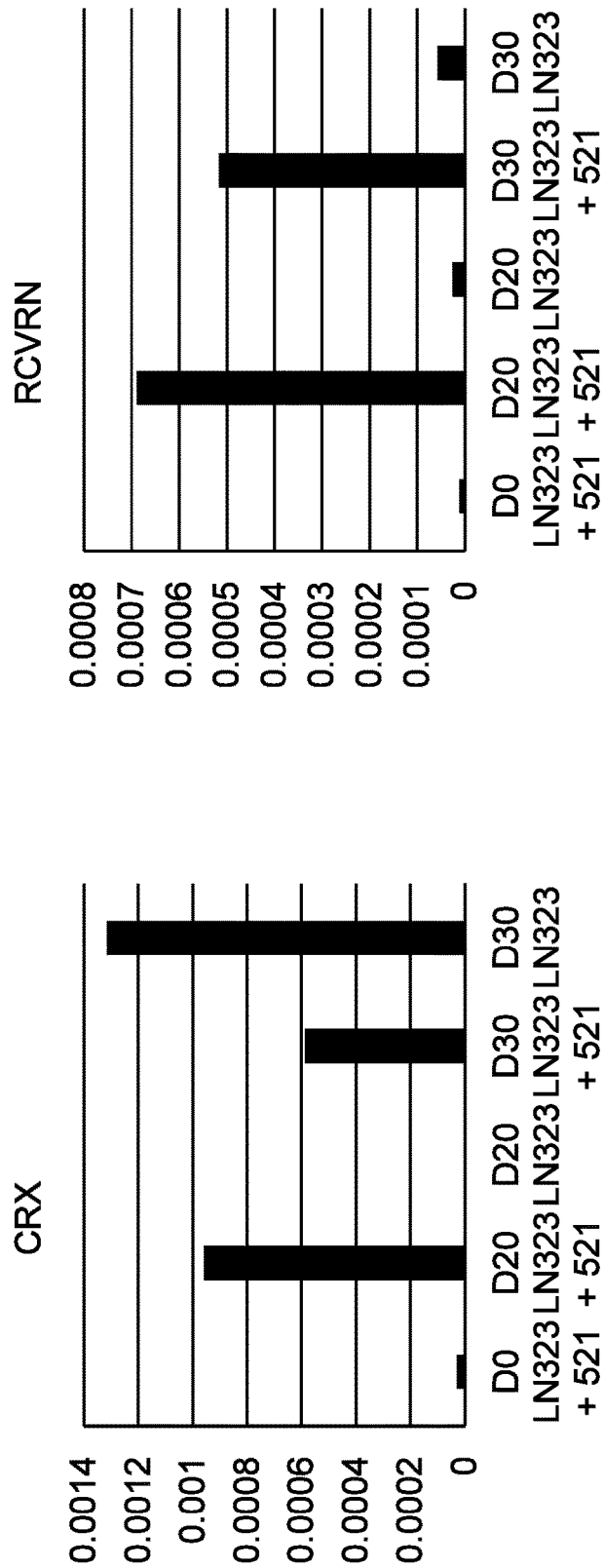

FIG. 2D and FIG. 2E are a set of five different graphs for the cells grown on the LN-323+LN-521 substrate. In the top graph of FIG. 2D, the y-axis is in arbitrary units, and runs from 0 to 0.15 in increments of 0.05. The x-axis is, from left to right, OCT3/4, NANOG, BRA, MIXL1, SOX17, FOXA2, and PAX6.

In the bottom left graph of FIG. 2D labeled PAX6, the y-axis is in arbitrary units, and runs from 0 to 0.16 in increments of 0.02. The x-axis is, from left to right, D0 LN-323+LN-521, D20 LN-323+LN-521, D20 LN-323 only, D30 LN-323+LN-521, and D30 LN-323 only.

In the bottom right graph of FIG. 2D labeled VSX2, the y-axis is in arbitrary units, and runs from 0 to 0.05 in increments of 0.005. The x-axis is, from left to right, D0 LN-323+LN-521, D20 LN-323+LN-521, D20 LN-323 only, D30 LN-323+LN-521, and D30 LN-323 only.

In the left graph of FIG. 2E labeled CRX, the y-axis is in arbitrary units, and runs from 0 to 0.0014 in increments of 0.0002. The x-axis is, from left to right, D0 LN-323+LN-521, D20 LN323+LN-521, D20 LN-323 only, D30 LN-323+LN-521, and D30 LN-323 only.

In the right graph of FIG. 2E labeled RCVRN, the y-axis is in arbitrary units, and runs from 0 to 0.0008 in increments of 0.0001. The x-axis is, from left to right, D0 LN-323+LN-521, D20 LN-323+LN-521, D20 LN-323 only, D30 LN-323+LN-521, and D30 LN-323 only.

Figure 2F:
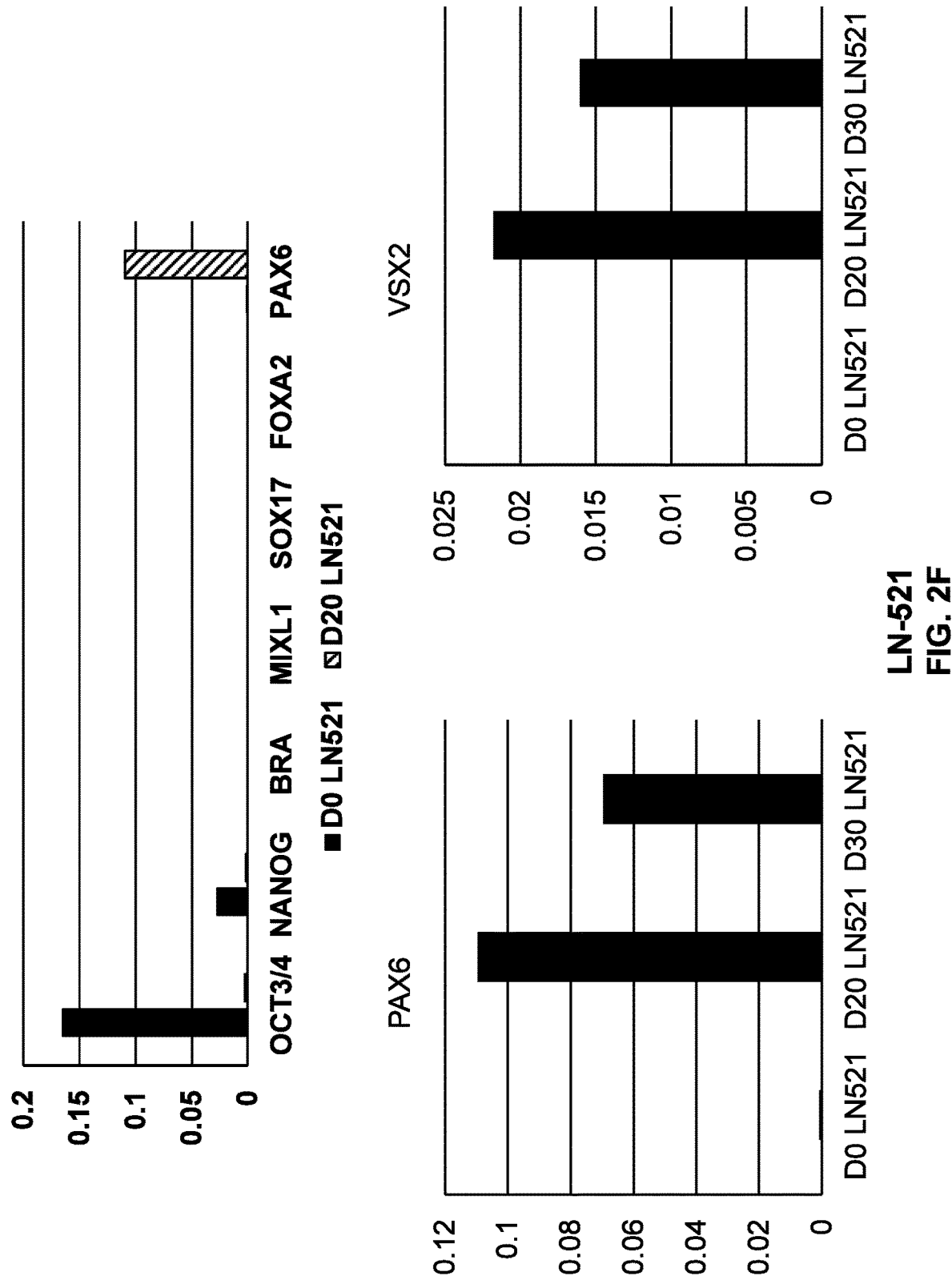
Figure 2G:
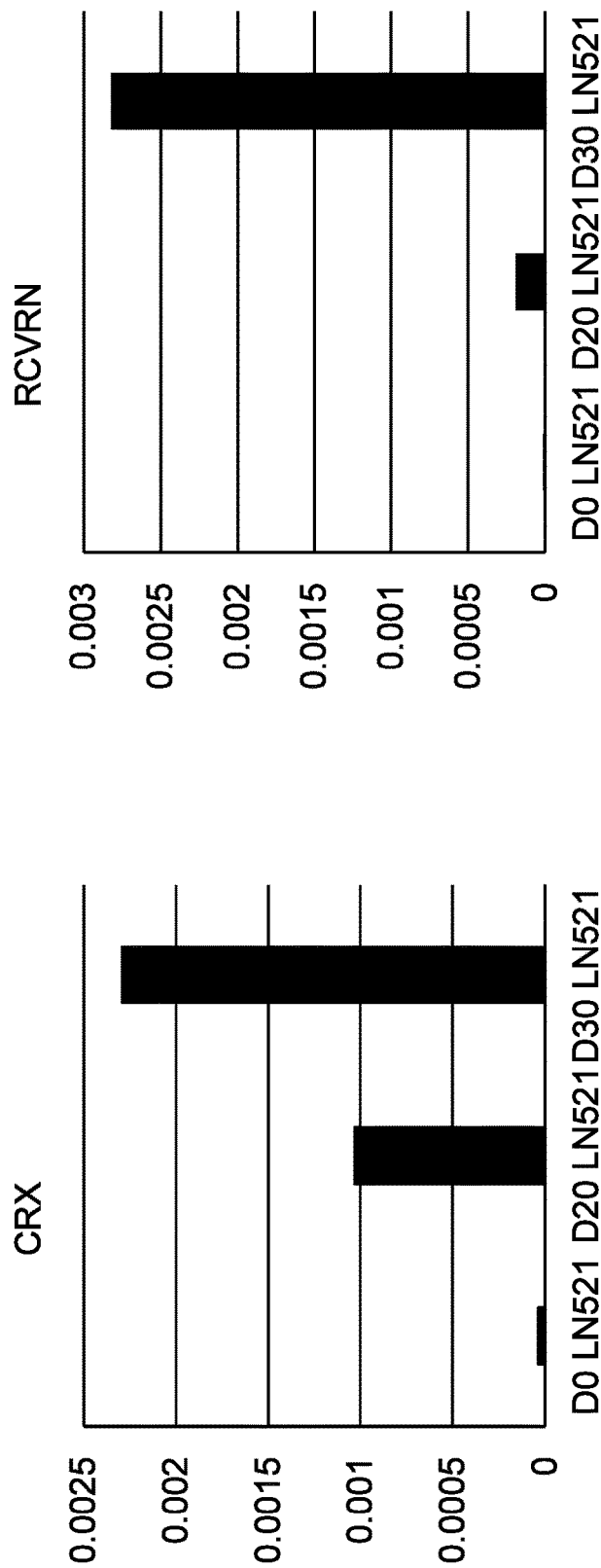

FIG. 2F and FIG. 2G are a set of five different graphs for the cells grown on a substrate of LN-521 only. In the top graph of FIG. 2F, the y-axis is in arbitrary units, and runs from 0 to 0.2 in increments of 0.05. The x-axis is, from left to right, OCT3/4, NANOG, BRA, MIXL1, SOX17, FOXA2, and PAX6.

In the bottom left graph of FIG. 2F labeled PAX6, the y-axis is in arbitrary units, and runs from 0 to 0.12 in increments of 0.02. The x-axis is, from left to right, D0 LN-521, D20 LN-521, and D30 LN-521.

In the bottom right graph of FIG. 2F labeled VSX2, the y-axis is in arbitrary units, and runs from 0 to 0.025 in increments of 0.005. The x-axis is, from left to right, D0 LN-521, D20 LN-521, and D30 LN-521.

In the bottom left graph of FIG. 2G labeled CRX, the y-axis is in arbitrary units, and runs from 0 to 0.0025 in increments of 0.0005. The x-axis is, from left to right, D0 LN521, D20 LN-521, and D30 LN-521.

In the bottom right graph of FIG. 2G labeled RCVRN, the y-axis is in arbitrary units, and runs from 0 to 0.003 in increments of 0.005. The x-axis is, from left to right, D0 LN-521, D20 LN-521, and D30 LN-521.

Figure 3C:
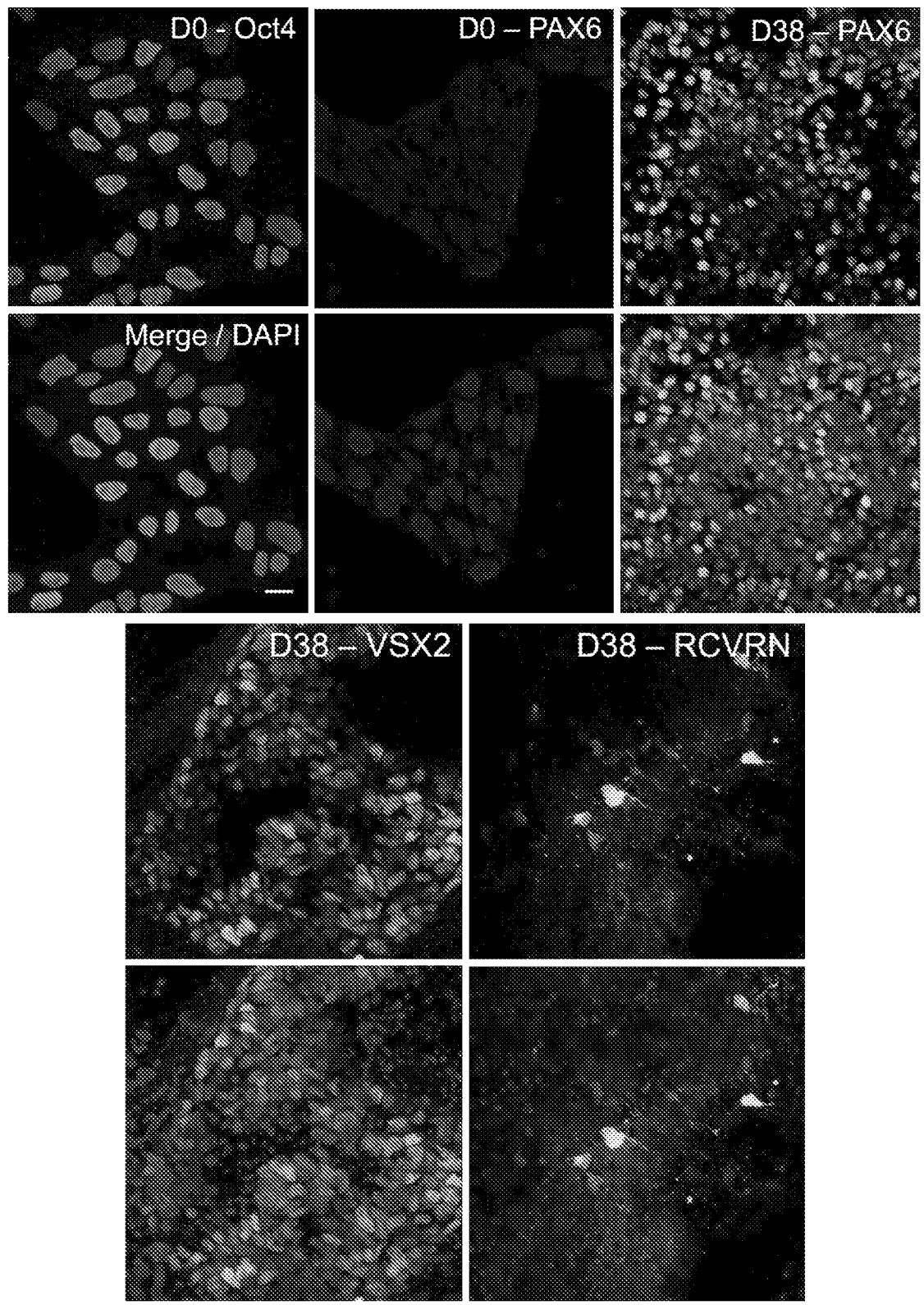

FIGS. 3A-3C are sets of pictures showing immunocytochemical analysis of D0 undifferentiated hESCs and D38 hESC-derived retinal cells. FIG. 3A is for cells grown on the LN-523+LN-521 substrate. FIG. 3B is for cells grown on the LN-523+LN-521 substrate. FIG. 3C is for cells grown on a substrate of only LN-521. Each set contains 10 micrographs, with scale bar=20 µm. In each set, the top row shows the analysis of D0 cells for OCT4, D0 cells for PAX6, and D38 cells for PAX6. The second row shows these merged with DAPI. The third row shows analysis of D38 cells for VSX2 and D38 cells for RCVRN. The fourth row shows these merged with DAPI. In D0 undifferentiated stem cells, OCT4 is expressed, but PAX6 (Paired box 6) is not. In the D38 differentiated cells, the markers PAX6, VSX2, and RCVRN are expressed.

Figure 3D:
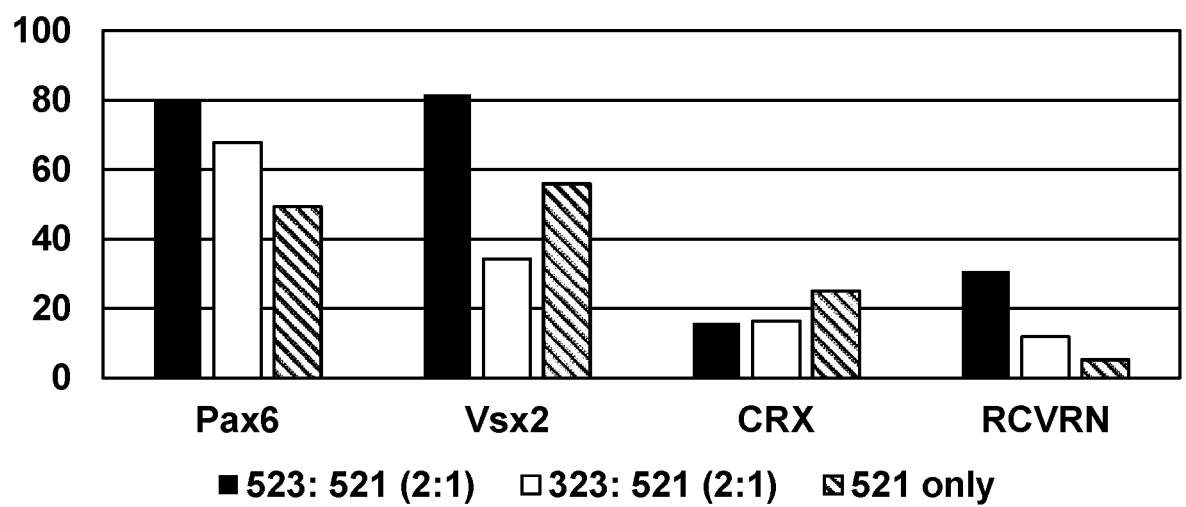

FIG. 3D is a bar graph comparing the expression of the markers PAX6, VSX2, CRX, and RCVRN across three laminin matrices. The y-axis is in arbitrary units, and runs from 0 to 100 in increments of 20. On the x-axis, from left to right, the markers are PAX6, VSX2, CRX, and RCVRN. For each marker, the left bar is expression on the LN-523:LN-521 substrate, the middle bar is for the LN-323:LN-521 substrate, and the right bar is for the LN-521 only substrate.

Figures 4A, 4B:
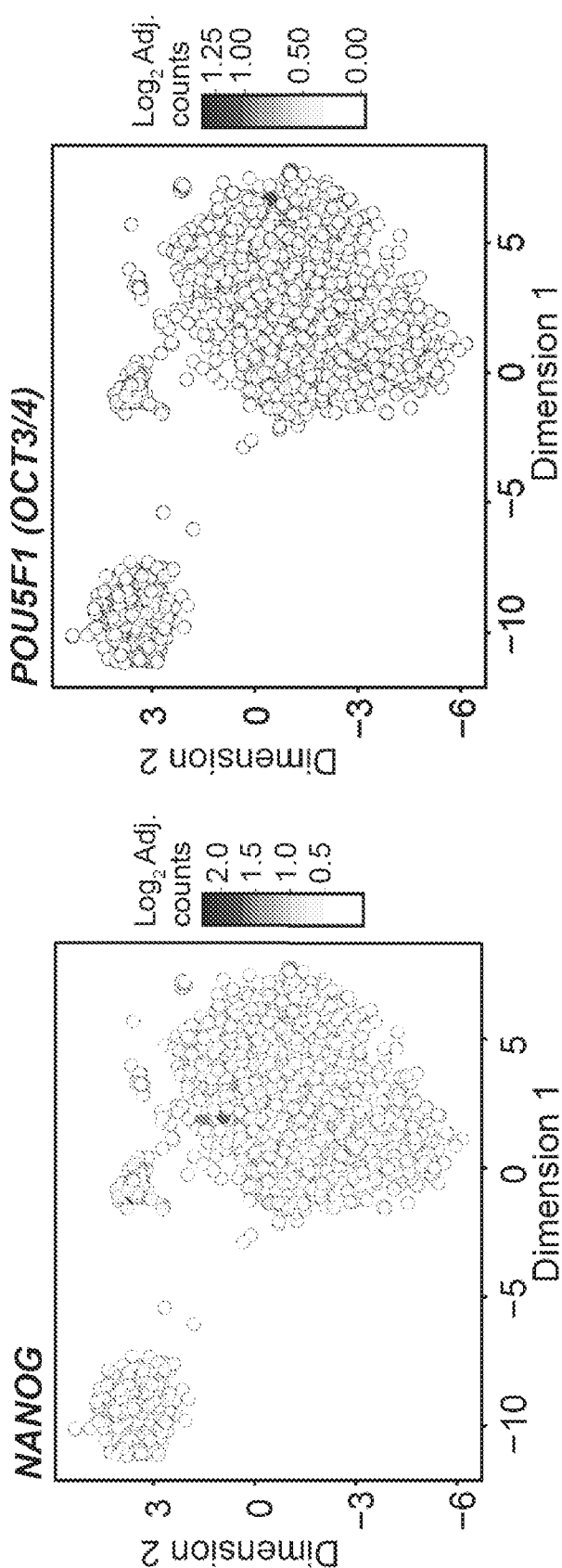

FIG. 4A is a t-distributed Stochastic Neighbor Embedding algorithm (t-SNE) visualization (t-SNE dimensions 1 and 2, x and y axis respectively) of the NANOG expression level for all Day 20 retinal progenitor cells profiled by single cell RNA-sequencing. Each dot represents a cell. "Log2 Adj. counts" refers to Log2 scran-normalized and cell cycle adjusted gene counts of NANOG. NANOG gene counts range from 0 to 2.21.

FIG. 4B is a t-SNE visualization of the POU5F1 expression level for all Day 20 retinal progenitor cells profiled by single cell RNA-sequencing. Each dot represents a cell. POU5F1 gene counts range from 0 to 1.33.

Figures 4C, 4D:
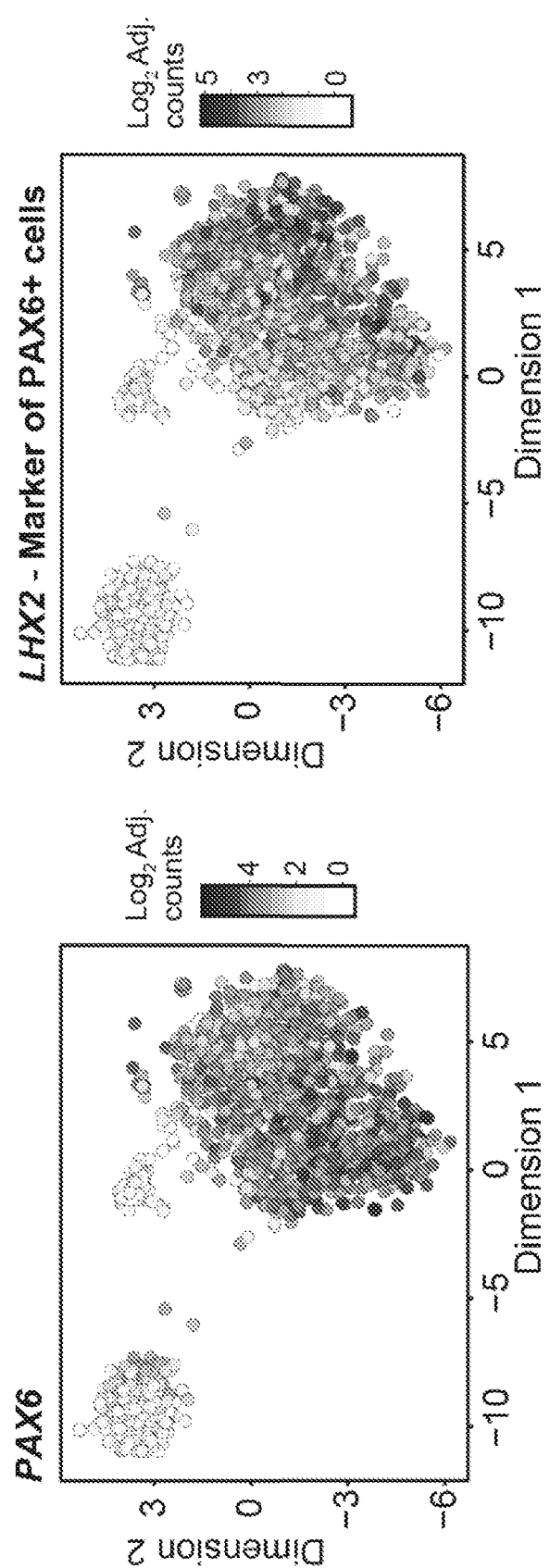

FIG. 4C is a t-SNE visualization of the PAX6 expression level for all Day 20 retinal progenitor cells profiled by single cell RNA-sequencing. Each dot represents a cell. PAX6 gene counts range from −0.36 to 5.87.

FIG. 4D is a t-SNE visualization of the LHX2 expression level for all Day 20 retinal progenitor cells profiled by single cell RNA-sequencing. Each dot represents a cell. LHX2 gene counts range from −0.54 to 5.00.

FIG. 5 is a heatmap showing the gene-gene expression (profiled by single-cell RNA-sequencing) pairwise correlation level, of the marker genes identified for the subpopulation of Day 20 retinal progenitor cells that express PAX6. This gene-gene expression pairwise correlation is computed across all Day 20 retinal progenitor cells profiled by single-cell sequencing and which passed the quality control steps. The level bar displays pairwise gene-gene expression pairwise Pearson correlation and ranges from −1 to 1.

Figure 6:
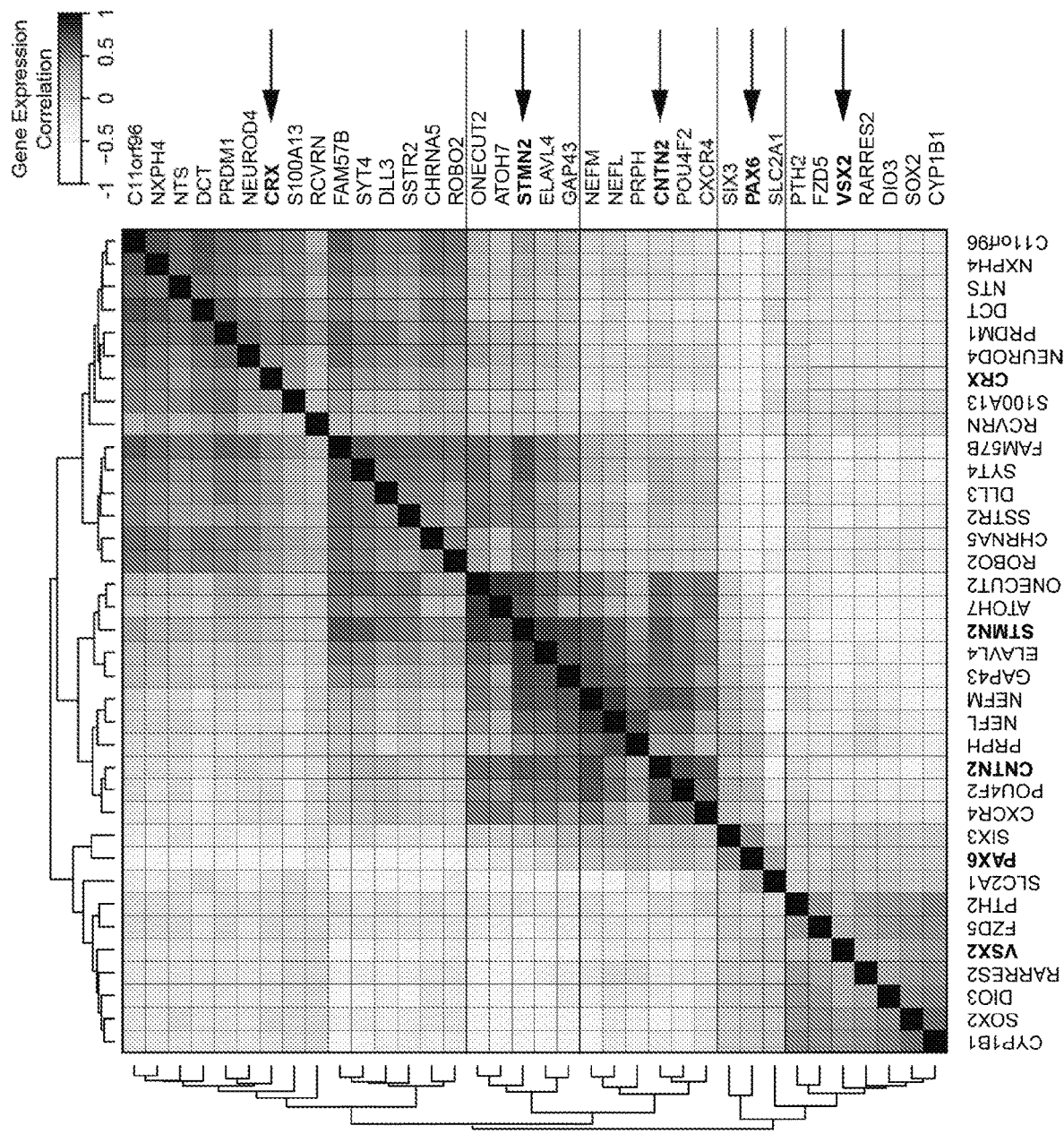

FIG. 6 is a heatmap showing the gene-gene expression (profiled by single-cell RNA-sequencing) pairwise correlation level, of the marker genes identified for each of the five subpopulation of cells identified within all Day 30 retinal progenitor cells. This gene-gene expression pairwise correlation is computed across all Day 30 retinal progenitor cells profiled by single-cell sequencing and which passed the quality control steps. From top to bottom the five subpopulation of cells are denoted as: CRX+, STMN2+, CNTN2+, PAX6+ and VSX2+. Marker genes belonging to the distinct subpopulation of cells are separated with lines. The genes naming each of the five subpopulation of cells are indicated with an arrow. The level bar displays gene-gene expression pairwise Pearson correlation and ranges from −1 to 1.

For reference, the vertical list of genes on the right-hand side in FIG. 6 reads as follows (from top to bottom): C11orf96; NXPH4; NTS; DCT; PRDM1; NEUROD4; CRX; S100A13; RCVRN; FAM57B; SYT4; DLL3; SSTR2; CHRNA5; ROBO2; ONECUT2; ATOH7; STMN2; ELAVL4; GAP43; NEFM; NEFL; PRPH; CNTN2; POU4F2; CXCR4; SIX3; PAX6; SLC2A1; PTH2; FZD5; VSX2; RARRES2; D103; SOX2; and CYP1B1. The horizontal list of genes on the bottom of FIG. 6 is the same, when read from right-to-left.

Figures 7A, 7B:
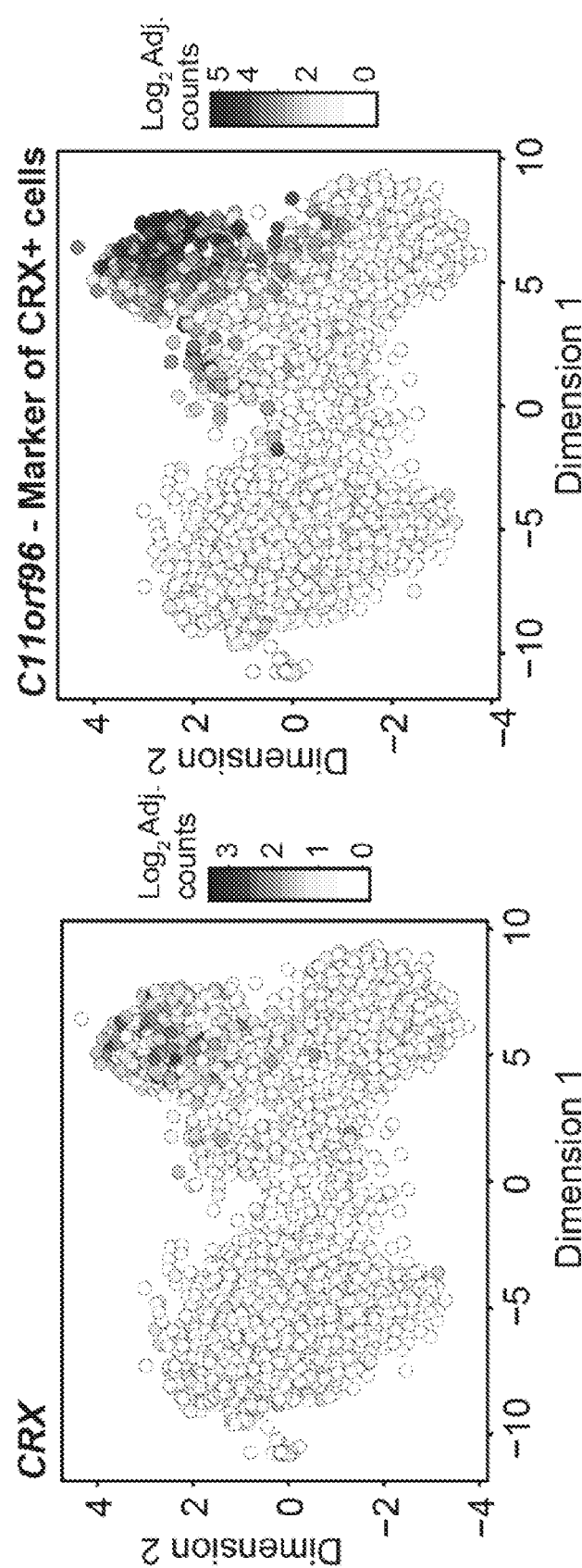

FIG. 7A is a t-distributed Stochastic Neighbor Embedding algorithm (t-SNE) visualization (t-SNE dimensions 1 and 2, x and y axis respectively) of the CRX expression level for all Day 30 retinal progenitor cells profiled by single cell RNA-sequencing. Each dot represents a cell. Log2 Adj. counts refers to Log2 scran-normalized and cell cycle adjusted gene counts. CRX gene counts range from −0.05 to 3.33.

FIG. 7B is a t-SNE visualization of the C11orf96 expression level for all Day 30 retinal progenitor cells profiled by single cell RNA-sequencing. Each dot represents a cell. C11orf96 gene counts range from −0.25 to 5.15.

Figures 7C, 7D:
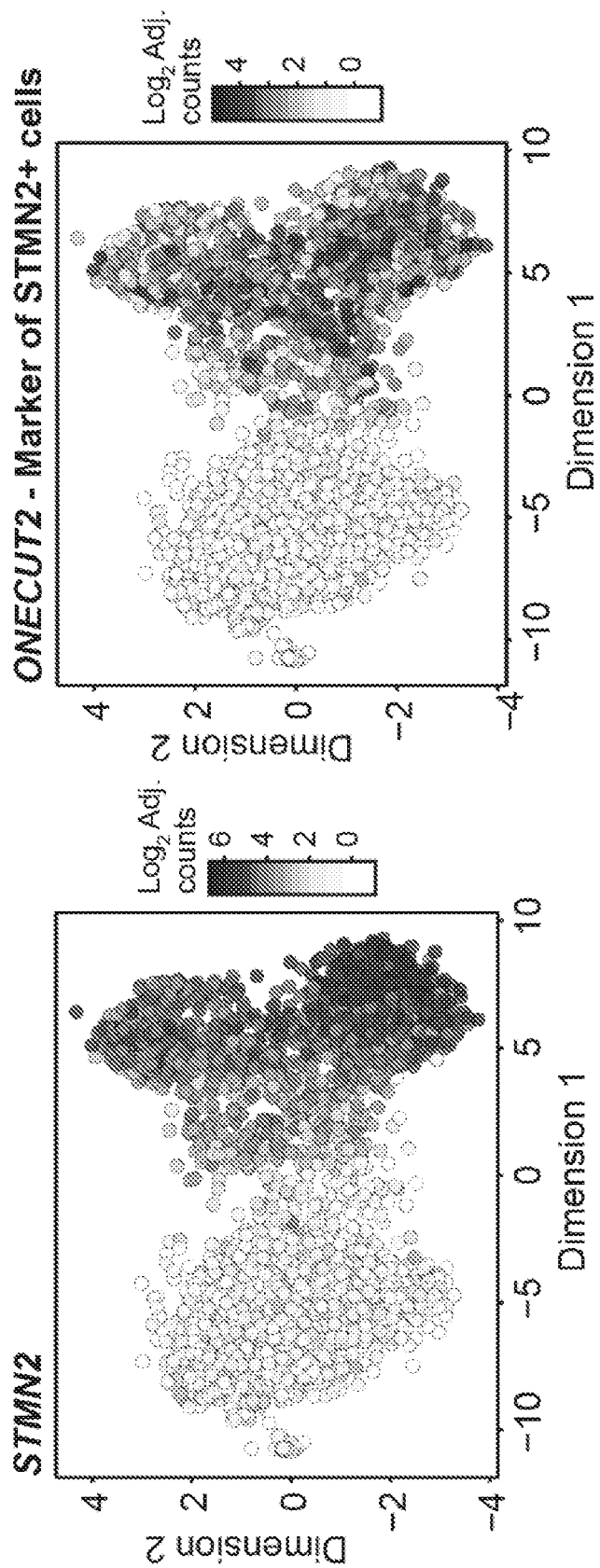

FIG. 7C is a t-SNE visualization of the STMN2 expression level for all Day 30 retinal progenitor cells profiled by single cell RNA-sequencing. Each dot represents a cell. STMN2 gene counts range from −0.92 to 6.52.

FIG. 7D is a t-SNE visualization of the ONECUT2 expression level for all Day 30 retinal progenitor cells profiled by single cell RNA-sequencing. Each dot represents a cell. ONECUT2 gene counts range from −0.80 to 4.81.

FIG. 7E is a t-SNE visualization of the CNTN2 expression level for all Day 30 retinal progenitor cells profiled by single cell RNA-sequencing. Each dot represents a cell. CNTN2 gene counts range from −0.24 to 5.35.

FIG. 7F is a t-SNE visualization of the POU4F2 expression level for all Day 30 retinal progenitor cells profiled by single cell RNA-sequencing. Each dot represents a cell. POU4F2 gene counts range from −0.14 to 4.47.

Figures 7G, 7H:
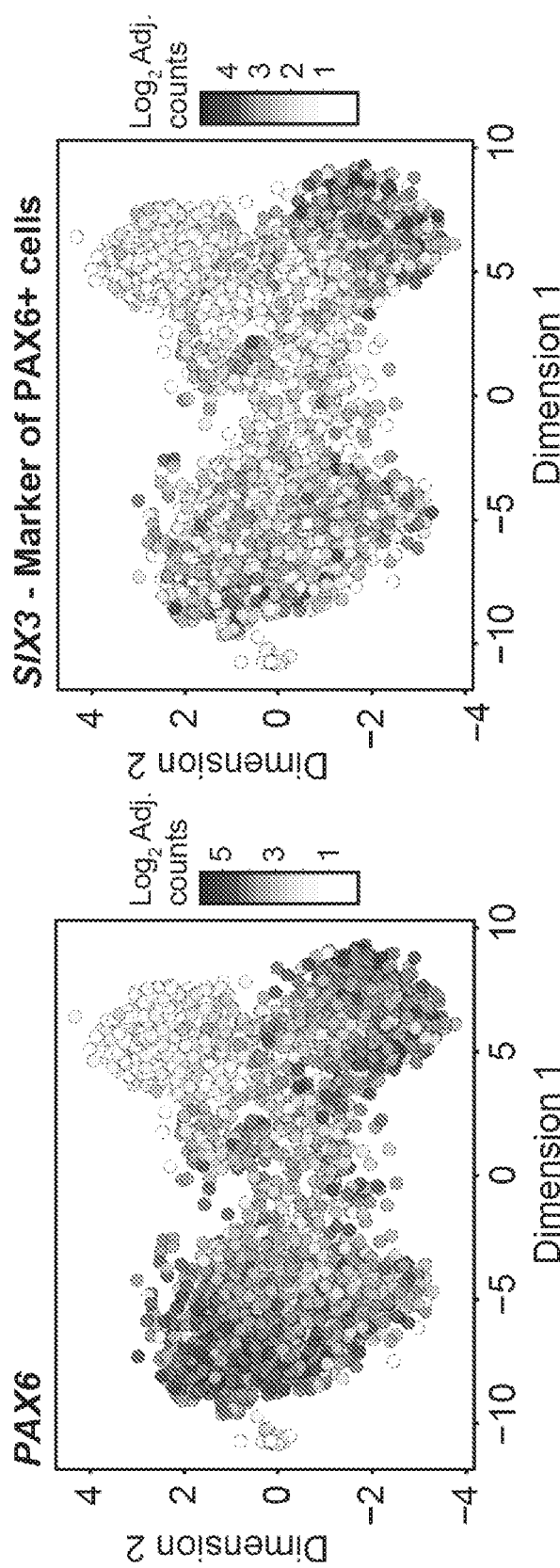

FIG. 7G is a t-SNE visualization of the PAX6 expression level for all Day 30 retinal progenitor cells profiled by single cell RNA-sequencing. Each dot represents a cell. PAX6 gene counts range from 0 to 5.68.

FIG. 7H is a t-SNE visualization of the SIX3 expression level for all Day 30 retinal progenitor cells profiled by single cell RNA-sequencing. Each dot represents a cell. SIX3 gene counts range from 0 to 4.63.

Figures 7I, 7J:
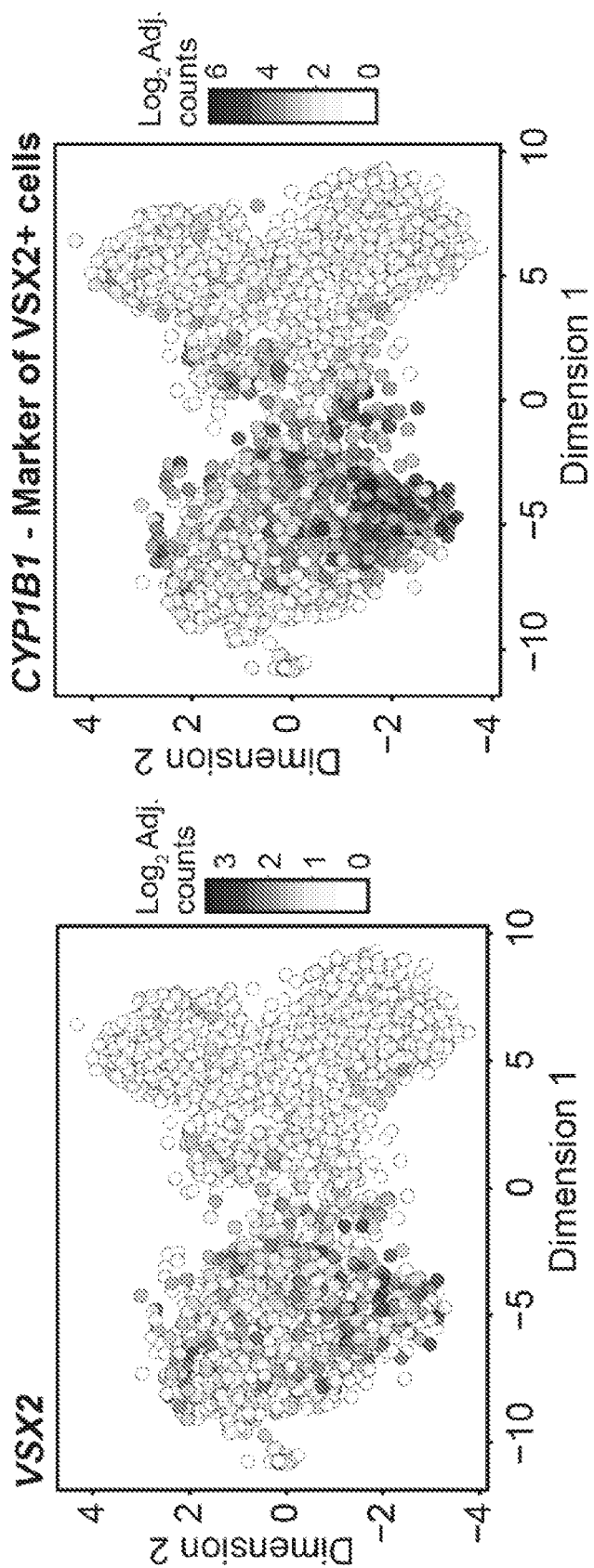

FIG. 7I is a t-SNE visualization of the VSX2 expression level for all Day 30 retinal progenitor cells profiled by single cell RNA-sequencing. Each dot represents a cell. VSX2 gene counts range from −0.17 to 3.28.

FIG. 7J is a t-SNE visualization of the CYP1B1 expression level for all Day 30 retinal progenitor cells profiled by single cell RNA-sequencing. Each dot represents a cell. CYP1B1 gene counts range from −0.23 to 6.01.

DETAILED DESCRIPTION

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

All publications, patents, and patent applications discussed herein are hereby incorporated by reference in their entirety.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

Several well-known references that may be relevant to the present disclosure include: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, Second Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), or the Ambion 1998 Catalog (Ambion, Austin, Tex.), Functional Diversity of Laminins, Domogatskaya, A, Rodin, S and Tryggvason, K., Annu. Rev. Cell Dev. Biol. 2012, 28, 523-553.

A laminin protein comprises one α-chain subunit, one β-chain subunit, and one γ-chain subunit, all joined together in a trimer through a coiled-coil domain. The twelve known laminin subunit chains can theoretically form at least 60 different isoforms. Currently, 16 trimeric laminin types have been identified in native mammalian tissues. Within the trimeric laminin structures are identifiable domains that possess binding activity towards other laminin and basal lamina molecules, as well as cell plasma membrane-bound receptors. For example, domains VI, IVb, and IVa form globular structures, and domains V, IIIb, and IIIa (which contain cysteine-rich EGF-like elements) for rod-like structures. Domains I and II at the C-terminus of the three chains participate in the formation of a triple-stranded coiled-coil structure (the long arm). There exist five genetically different alpha chains, three beta chains, and three gamma chains that have been found in human tissues in at least sixteen different combinations. One nomenclature for these laminin proteins describes the isoforms based on their chain compositions, e.g., laminin-111 contains alpha-1, beta-1, and gamma-1 chains.

As used herein, the term "laminin-323" (LN-323) refers to the protein formed by joining α3, β2 and γ3 chains together. As used herein, the term "laminin-521" (LN-521) refers to the protein formed by joining α5, β2 and γ1 chains together. As used herein, the term "laminin-523" (LN-523) refers to the protein formed by joining α5, β2 and γ3 chains together. These terms should be construed as encompassing both the recombinant laminin and heterotrimeric laminin from naturally occurring sources. The term "recombinant" indicates that the protein is artificially produced using expression plasmids in cells that do not normally express such proteins.

The laminin can be a complete protein trimer, or a protein chain, or a protein fragment. The term "complete" refers to the protein being composed of all the domains of the α-chain, one β-chain, and γ-chain, with the three chains being joined together to form the heterotrimeric structure. The protein is not broken down into separate chains, fragments, or functional domains. The term "chain" refers to the entirety of the individual alpha, beta, or gamma chain of the laminin protein. The term "fragment" refers to any protein fragment that contains one, two, or three functional domains that possesses binding activity to another molecule or receptor. However, a chain should not be considered a fragment because each chain possesses more than three such domains. Similarly, a complete laminin protein trimer should not be considered a fragment. Examples of functional domains include Domains I, II, III, IV, V, VI, and the G domain. Further information on these domains is found in Domogatskaya, A., Rodin, S., and Tryggvason, K. 2012. Functional diversity of laminins. *Annu Rev Cell Dev Biol* 28:523-553, which is incorporated by reference.

The present disclosure relates to methods for culturing and differentiating pluripotent stem cells to obtain retinal progenitor cells (such as photoreceptor progenitor cells or ganglion progenitor cells) or retinal photoreceptor cells. In particular, the stem cells are cultured on a laminin matrix that contains only two laminin isoforms. The first laminin in the laminin matrix is LN-323 or LN-523, which are located in the matrix surrounding the retinal photoreceptors in vivo. The second laminin in the laminin matrix is LN-521. Alternatively, the laminin matrix can contain only a single laminin, which is laminin-521. The stem cells are then exposed to two particular cell culture mediums. This results in pluripotent stem cell derived photoreceptors that are more suitable for clinical applications than cells grown on substrates containing an undefined, xenogenic and alternative blend of extracellular matrices.

Differentiated cells typically require two things to survive and reproduce: (1) a substrate that provides a structural and phenotype stabilizing support for the cell; and (2) a cell culture medium to provide nutrition to the cells. Very generally, the pluripotent stem cells are cultured on a laminin matrix which can be affixed to a solid surface, which acts as a structural support and which also maintains the pluripotent phenotype. The term "solid" refers to the state of matter, i.e. the substrate is not liquid or gas or plasma. The surface can be rigid/hard or very flexible (such as a film), and the term "solid" should not be construed as requiring a particular degree of rigidity. The surface (1) is typically a container, for example a petri dish or in the well of a multi-well plate. The laminin matrix is in the form of a substrate (i.e. a layer or a coating) upon the surface. Application of different cell culture media at appropriate time intervals in combination with the substrates containing two laminins results in differentiated photoreceptors (either as progenitor cells or as mature cells).

The stem cells that can be used with the methods and materials disclosed herein are pluripotent human stem cells. Such stem cells can include induced pluripotent stem cells, embryonic stem cells, adult stem cells, fetal stem cells, amniotic stem cells, and generally any pluripotent stem cell. A stem cell is an undifferentiated cell from which specialized cells are subsequently derived. Pluripotency refers to a cell that has the potential to differentiate into cells of all three germ layers.

In some embodiments, the laminin matrix contains a mixture of two laminins. The laminin matrix contains only two laminin trimers/chains/fragments, but permits other ingredients to still be present in the laminin matrix. The first laminin is either laminin-323 (LN-323) or laminin-523 (LN-523). The second laminin is laminin-521 (LN-521). Each laminin can be an intact protein or a protein fragment, although in preferred embodiments the laminins are intact proteins.

In particular embodiments, it is contemplated that the weight ratio of the laminin-323/523 to the laminin-521 in the laminin matrix is from about 1:1 to about 4:1, including from about 1:1 to about 2:1 (i.e. always less laminin-521 than the laminin-323/523). In particular, laminin-323 and laminin-523 are present in the external limiting membrane spanning the rods and cones in the retina, and laminin-523 is present in the Bruch's membrane located beneath the RPE. Their presence is believed to drive the differentiation of the stem cells into retinal lineage specific cells.

In other embodiments, the laminin matrix contains only a single laminin, which is laminin-521. Other ingredients (besides laminins) may still be present in the laminin matrix.

The cell culture substrate is used in combination with multiple cell culture mediums to obtain the desired retinal progenitor cells or photoreceptor cells. Two different cell culture mediums are used, which are described below and referred to herein as neural induction medium and photoreceptor differentiation medium.

The neural induction medium and the photoreceptor differentiation medium both start with a basal medium. The basal medium consists of Glasgow minimum essential medium (GMEM), which is available from ThermoFisher Scientific (catalog no. 11710035). The GMEM is supplemented with 0.1 mM of β-mercaptoethanol, 1x of Non-Essential Amino Acid Solution (Gibco catalog no. 11140050, provided as 100x), and 1 mM of pyruvate to make the basal medium.

For reference, GMEM contains the following ingredients listed in Table 1:

TABLE 1

| GMEM Ingredient | Concentration (mg/L) | GMEM Ingredient | Concentration (mg/L) |
|---|---|---|---|
| L-Arginine hydrochloride | 42.0 | Folic Acid | 2.0 |
| L-Cystine 2HCl | 31.0 | Niacinamide | 2.0 |
| L-Glutamine | 292.0 | Pyridoxal hydrochloride | 2.0 |
| L-Histidine hydrochloride-$H_2O$ | 21.0 | Riboflavin | 0.2 |
| L-Isoleucine | 52.0 | Thiamine hydrochloride | 2.0 |
| L-Leucine | 52.0 | i-Inositol | 3.6 |
| L-Lysine hydrochloride | 73.0 | Calcium Chloride ($CaCl_2$) (anhyd.) | 200.0 |
| L-Methionine | 15.0 | Ferric Nitrate ($Fe(NO_3)_3$—$9H_2O$) | 0.1 |
| L-Phenylalanine | 33.0 | Magnesium Sulfate ($MgSO_4$) (anhyd.) | 97.67 |
| L-Threonine | 47.6 | Potassium Chloride (KCl) | 400.0 |
| L-Tryptophan | 8.0 | Sodium Bicarbonate ($NaHCO_3$) | 2750.0 |
| L-Tyrosine disodium salt dihydrate | 52.0 | Sodium Chloride (NaCl) | 6400.0 |
| L-Valine | 46.8 | Sodium Phosphate monobasic ($NaH_2PO_4$—$H_2O$) | 124.0 |
| Choline chloride | 2.0 | D-Glucose (Dextrose) | 4500.0 |
| D-Calcium pantothenate | 2.0 | Phenol Red | 15.0 |

1× of Non-Essential Amino Acid Solution contains the following ingredients in the concentration listed in Table 2:

TABLE 2

| 1x Ingredient | Concentration (mg/L) |
|---|---|
| Glycine | 7.5 |
| L-Alanine | 8.9 |
| L-Asparagine | 13.20 |
| L-Aspartic acid | 13.30 |
| L-Glutamic Acid | 14.70 |
| L-Proline | 11.50 |
| L-Serine | 10.50 |

The neural induction medium and the photoreceptor differentiation medium are made by mixing parts by volume of the basal medium with other additives. One such additive is B27 Supplement without vitamin A, which can be obtained from Thermo Fisher (catalog no. 12587010, offered at 50×). Another additive is N2 supplement, which can be obtained from Thermo Fisher (catalog no. A1370701, offered at 100×). Other additives include human brain-derived neurotrophic factor (BDNF), human ciliary neurotrophic factor (CNTF), retinoic acid, a TGFβ inhibitor such as SB431542 (CAS #301836-41-9), a gamma-secretase inhibitor such as DAPT. BDNF can be obtained from Peprotech (catalog no. 450-02), and a Wnt inhibitor such as CKI-7. CNTF can be obtained from Prospec-Tany Technogene (catalog no. CYT-272). DAPT can be obtained from Selleckchem (catalog no. S2215). CKI-7 can be obtained from Sigma (CAS #1177141-67-1, catalog no. C0742).

The neural induction medium is made by mixing 97 parts by volume (pbv) of the basal medium with 2 pbv of the B27 Supplement without vitamin A and 1 pbv of N2 supplement, and then adding a TGFβ inhibitor (such as SB431542) and a Wnt inhibitor. The TGF-β inhibitor is present in a concentration of about 1 μM to about 10 μM, and in particular about 5 μM. In specific embodiments, the TGF-β inhibitor is SB431542. The Wnt inhibitor is present in a concentration of about 1 μM to about 10 μM, and in particular about 5 μM. In specific embodiments, the Wnt inhibitor is CKI-7. The neural induction medium does not include growth factors such as BDNF, CNTF, or gamma secretase inhibitor.

The photoreceptor differentiation medium is made by mixing 97 parts by volume (pbv) of the basal medium with 2 pbv of the B27 Supplement without vitamin A and 1 pbv of N2 supplement, and then adding BDNF, CNTF, retinoic acid, and a gamma secretase inhibitor (such as DAPT). The BDNF is present in a concentration of about 1 ng/mL to about 20 ng/mL, and in particular about 10 ng/mL. The CNTF is present in a concentration of about 1 ng/mL to about 30 ng/mL, including from about 5 ng/mL to about 25 ng/mL, or from about 10 ng/mL to about 20 ng/mL, and in particular about 20 ng/mL. The retinoic acid is present in a concentration of about 0.1 μM to about 5 μM, and in particular about 0.5 μM. The gamma secretase inhibitor is present in a concentration of about 5 μM to about 15 μM, and in particular about 10 μM. The photoreceptor differentiation medium does not include TGFβ inhibitor or Wnt inhibitor.

The stem cells are first plated onto the laminin matrix/cell culture substrate made up of one or two laminins as described above. The stem cells are typically applied as a monolayer, and can be plated at a density of about 10,000 cells per $cm^2$.

Differentiation is then initiated by applying the neural induction medium to the plated stem cells. The cells are cultured in the neural induction medium for a first time period of about 120 hours to about 168 hours, including about 144 hours (i.e. 6 days). The medium may be periodically changed, for example every 48 hours.

Next, the neural induction medium is removed, and the photoreceptor differentiation medium is applied to the plated stem cells. The cells are cultured in the photoreceptor differentiation medium for a second time period of about 288 hours (12 days) to about 816 hours (34 days). The medium may be periodically changed, for example every 48 hours. The length of time of exposure to the photoreceptor differentiation medium will affect the maturity of the resulting cells, such that retinal progenitor cells or mature photoreceptor cells can be obtained. This results in a total time period of about 20 days to about 40 days of differentiation and maturation to obtain the desired retinal photoreceptor cells (progenitors or mature). The photoreceptor cells can then be transplanted into one or both eyes of a patient, or used for other applications.

Differentiation from stem cells to the desired photoreceptor cells can be identified by significant downregulation of pluripotency markers Oct3/4 and Nanog, and upregulation of the marker PAX6 by day 20 after the start of differentiation. The markers VSX2, CRX, and RCVRN are upregulated on day 30 after the start of differentiation. These can be quantified by qPCR or immunostaining.

The methods disclosed herein are robust for differentiating human embryonic stem cells to photoreceptor cells in a chemically defined and xeno-free culture environment, with the prospect of transplanting clinically safe photoreceptors into patients. Thus, this provides chemically defined and animal serum-free methods that are GMP compatible and provide clinical grade photoreceptor cells.

Certain retinal progenitor cell subpopulations can also be identified by the use of gene or protein profiles made on certain days after the start of differentiation. A "Day X gene profile" contains the gene expression level of the progenitor cell on Day X, with the gene expression level being measured in units of gene counts per million (CPM), as computed by the function calculateCPM from the scater 1.8.4 R package. In this regard, it is expected that the expression level of a given gene will vary during the differentiation process, and measurements of expression levels can be used to identify subpopulations that may be particularly useful for a particular purpose.

Four particular gene profiles are contemplated. The first gene profile is made on any one of Days 16-24, also referred to herein as a "Day 16-24 gene profile." The second gene profile is made on Day 20, also referred to herein as a "Day 20 gene profile." Any reference to a Day 16-24 gene profile should also be considered as referring specifically to a Day 20 gene profile. The third gene profile is made on any one of Days 26-34, also referred to herein as a "Day 26-34 gene profile." The fourth gene profile is made on Day 30, also referred to herein as a "Day 30 gene profile." Any reference to a Day 26-34 gene profile should also be considered as referring specifically to a Day 30 gene profile.

Five particular subpopulations have been identified, based on the Day 16-24 gene profile and the Day 26-34 gene profile.

In the first subpopulation (A), at least one of genes CRX, C11orf96, NXPH4, NTS, DCT, PRDM1, NEUROD4, S100A13, RCVRN, FAM57B, SYT4, DLL3, SSTR2, CHRNA5, and ROBO2 is expressed in the Day 26-34 gene profile. Combinations of any 2, 3, 4, 5, 6, 7, 8, 9, 10, 11, 12, 13, 14, or 15 of these genes are specifically contemplated. In some embodiments, the combination of expressed genes includes CRX and C11orf96.

In the second subpopulation (B), at least one of genes STMN2, ONECUT2, ATOH7, ELAVL4, and GAP43 is expressed in the Day 26-34 gene profile. Combinations of any 2, 3, 4, or 5 of these genes are specifically contemplated. In some embodiments, the combination of expressed genes includes STMN2 and ONECUT2.

In the third subpopulation (C), at least one of genes CNTN2, NEFM, NEFL, PRPH, POU4F2, and CXCR4 is expressed in the Day 26-34 gene profile. Combinations of any 2, 3, 4, 5, or 6 of these genes are specifically contemplated. In some embodiments, the combination of expressed genes includes CNTN2 and POU4F2.

In the fourth subpopulation (D), at least one of genes PAX6, SIX3, and SLC2A1 is expressed in the Day 26-34 gene profile. Combinations of any 2 or 3 of these genes are specifically contemplated. In some embodiments, the combination of expressed genes includes PAX6 and SIX3.

In the fifth subpopulation (E), at least one of genes VSX2, PTH2, FZD5, RARRES2, DIO3, SOX2, and CYP1B1 is expressed in the Day 26-34 gene profile. Combinations of any 2, 3, 4, 5, 6, or 7 of these genes are specifically contemplated. In some embodiments, the combination of expressed genes includes VSX2 and CYP181.

In the present disclosure, reference to a gene being "expressed" means the gene expression level of that gene has a minimum value of 1 gene count-per-million (CPM). It is also noted that discussion of certain genes being expressed in these subpopulations should not be interpreted to mean that other genes are not expressed. For example, it is possible that gene STMN2 is still expressed in subpopulation (A).

In addition, in these five subpopulations, the Day 16-24 gene profile usually indicates that at least one of genes DAPL1, SIX6, SFRP2, LHX2, PAX6, CDH2, CLDN1, TRPM3, RELN, DCT, or PMEL is expressed. Combinations of any 2, 3, 4, 5, 6, 7, 8, 9, 10, or 11 of these genes are specifically contemplated. In more specific embodiments, at least one of genes SIX6, SFRP2, LHX2, PAX6, DCT, or PMEL is expressed, including combinations of any 2, 3, 4, 6, or 6 of these genes. In particular embodiments, PAX6 is expressed in the Day 16-24 gene profile. The Day 16-24 gene profile can be used, if desired, to discard differentiating cells that will not end in the desired cell lineage.

In particular embodiments of subpopulation (A), the Day 26-34 gene profile indicates that (i) CRX is expressed with at least 5 gene CPM, and/or (ii) C11orf96 is expressed with at least 5 gene CPM. In more specific embodiments, the Day 26-34 gene profile indicates that (i) CRX is expressed with at least 10 gene CPM, and/or (ii) C11orf96 is expressed with at least 10 gene CPM.

In particular embodiments of subpopulation (B), the Day 26-34 gene profile indicates that (i) STMN2 is expressed with at least 5 gene CPM, and/or (ii) ONECUT2 is expressed with at least 5 gene CPM. In more specific embodiments, the Day 26-34 gene profile indicates that (i) STMN2 is expressed with at least 10 gene CPM, and/or (ii) ONECUT2 is expressed with at least 10 gene CPM.

In particular embodiments of subpopulation (C), the Day 26-34 gene profile indicates that (i) CNTN2 is expressed with at least 5 gene CPM, and/or (ii) POU4F2 is expressed with at least 5 gene CPM. In more specific embodiments, the Day 26-34 gene profile indicates that (i) CNTN2 is expressed with at least 10 gene CPM, and/or (ii) POU4F2 is expressed with at least 10 gene CPM.

In particular embodiments of subpopulation (D), the Day 26-34 gene profile indicates that (i) PAX6 is expressed with at least 5 gene CPM, and/or (ii) SIX3 is expressed with at least 5 gene CPM. In more specific embodiments, the Day 26-34 gene profile indicates that (i) PAX6 is expressed with at least 10 gene CPM, and/or (ii) SIX3 is expressed with at least 10 gene CPM.

In particular embodiments of subpopulation (E), the Day 26-34 gene profile indicates that (i) VSX2 is expressed with at least 5 gene CPM, and/or (ii) CYP1B1 is expressed with at least 5 gene CPM. In more specific embodiments, the Day 26-34 gene profile indicates that (i) VSX2 is expressed with at least 10 gene CPM, and/or (ii) CYP1B1 is expressed with at least 10 gene CPM.

The present disclosure is further illustrated in the following non-limiting working examples, it being understood that these examples are intended to be illustrative only and that the disclosure is not intended to be limited to the materials, conditions, process parameters and the like recited herein.

EXAMPLES

Example 1

Cell Line Development of HEK Overexpressing LN-523 and LN-323

Figure 1A:
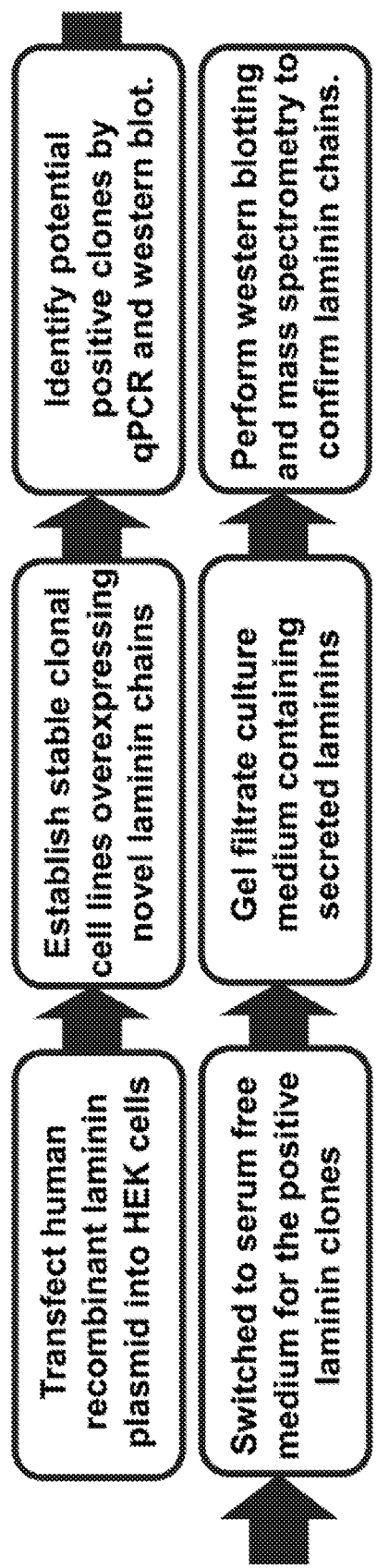
FIG. 1A is a flow chart describing the steps for producing recombinant laminin-523 and laminin-323 in some methods of the present disclosure.

A flow chart describing the steps for producing recombinant laminin-523 and laminin-323 is provided in FIG. 1A. Briefly, human recombinant laminin expression plasmids encoding laminin alpha-3, beta-2, and gamma-3 chains and containing three different antibiotic resistance genes were generated and sequentially transfected into HEK cells. For producing LN-523, expression plasmids encoding laminin alpha-5, beta-2, and gamma-3 chains were sequentially transfected into HEK cells. Stable clonal cell lines overexpressing the desired laminin chains were established. Third, potential positive clones were identified using qPCR and Western blot. Fourth, the cell culture medium was switched to a serum-free medium for the positive laminin clones. Fifth, cell culture medium containing secreted laminins was filtered through gel. Finally, Western blotting and mass spectrometry were performed to confirm the identities of the laminin chains.

Human Embryonic Kidney (HEK) 293 cells were cultured and maintained in a basal medium consisting of DMEM-GlutaMAX, high glucose, pyruvate (Life Technologies) and supplemented with 10% fetal calf serum in the presence of Pen-Strep (Life Technologies). For GMP production of human LN-323 and LN-523 for therapy purposes, the cells are cultured in the presence of human serum (instead of fetal calf serum).

Before plasmid transfection, HEK293 cells were seeded in the absence of Pen-Strep so that they will reach ~70% confluency at the time of transfection. Human recombinant laminin plasmid (pcDNA3.1) containing the Human laminin-gamma-3 chain was first transfected into HEK293 cells using Lipofectamine® 2000 reagent (Life Technologies) and Opti-MeM (Life Technologies). Clonal stable cell line HEK003 was first established using Hygromycin B selection with the use of cloning rings (Bel-Art). This was followed by transfection using plasmid expressing the laminin beta-2 chain into HEK003. HEK023 was subsequently established using Geneticin (G418) and Hygromycin B selections. Plasmid expressing laminin alpha-5 and laminin alpha-3 chain was separately transfected into HEK023 clonal cell line to generate HEK523 and HEK323 clonal cell lines, respectively. The final HEK523/323 cell line was selected by Zeocin, Geneticin (G418) and Hygromycin B.

The identities of the clonal cell lines were determined by quantitative polymerase chain reaction (qPCR) analyses using LAMA5, LAMA3, LAMB2 and LAMC3 gene primer pairs. The potential positive clonal cell lines of HEK523 and HEK323 were further expanded and the basal culture medium was switched to serum-free medium for a week. The medium was collected and western blot analysis was performed to further confirm the identity of the laminin protein produced by the positive clonal cell line. The selected positive HEK523 and HEK323 clonal cell lines should secrete LN-523 and LN-323 into the medium, respectively. Dialysis of the media was performed in polyethylene glycol for 4-5 days at 4° C. The LN-523 and LN-323 containing media were concentrated in Amico centrifugal tubes and protein purification was performed using AKTA chromatography system (GE Healthcare Life Sciences) through a XK26/100 column. Western blot and mass spectrophotometry were performed to analyze the eluted purified fractions of the retina specific laminin isoforms.

Figure 1B:
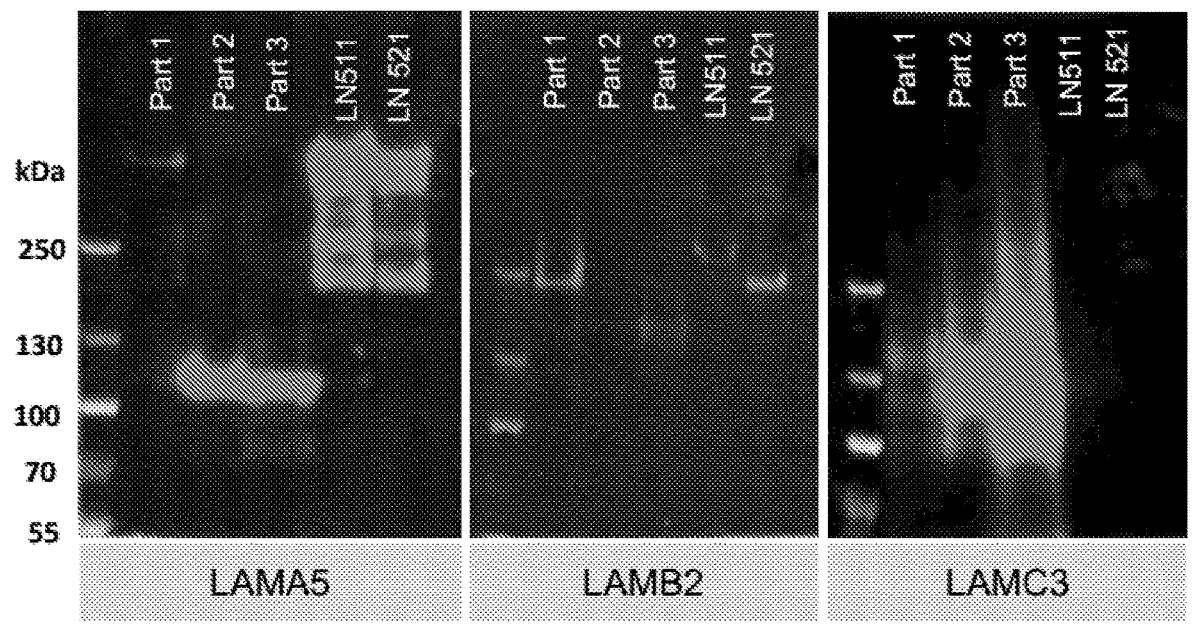
FIG. 1B is a Western blot showing the presence of LAMA5, LAMB2, and LAMC3 chains in the purified fractions or parts of LN-523.
Figure 1C:
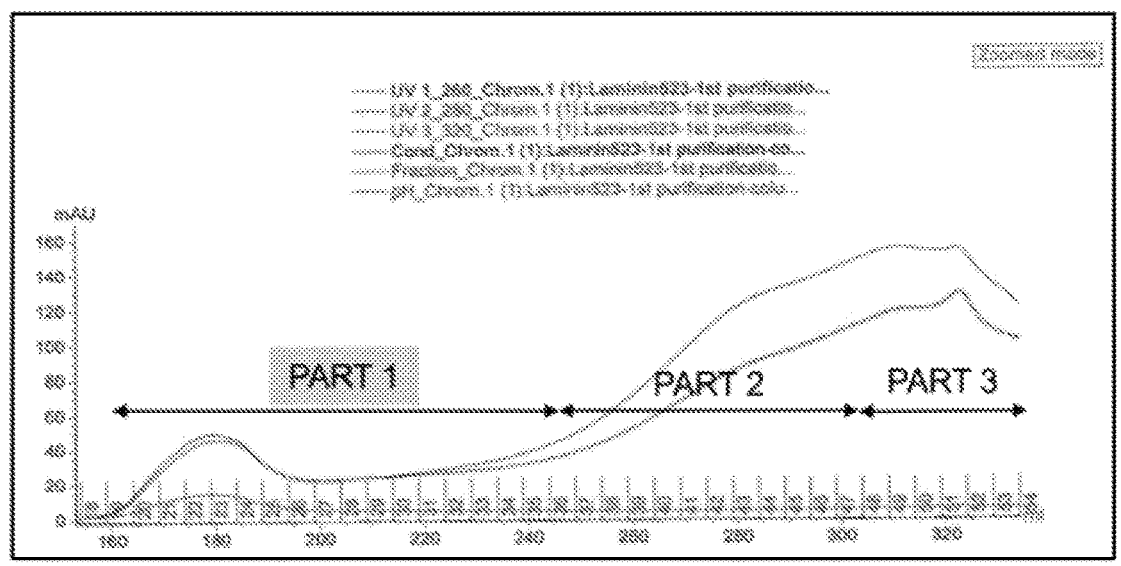
FIG. 1C is a chromatogram illustrating the protein elution profile of a LN-523 clone using the AKTA Chromatography System.

FIG. 1B is a Western blot showing the presence of laminin alpha-5, beta-2, and gamma-3 chains in the purified fractions or parts of LN-523. FIG. 1C is a chromatogram illustrating the protein elution profile of a LN-523 clone using the AKTA Chromatography System. FIG. 1D is LC-MS/MS (Liquid Chromatography-Mass Spectrophotometry) results showing that laminin alpha-5, beta-2, and gamma-3 chains are present.

Figure 1E:
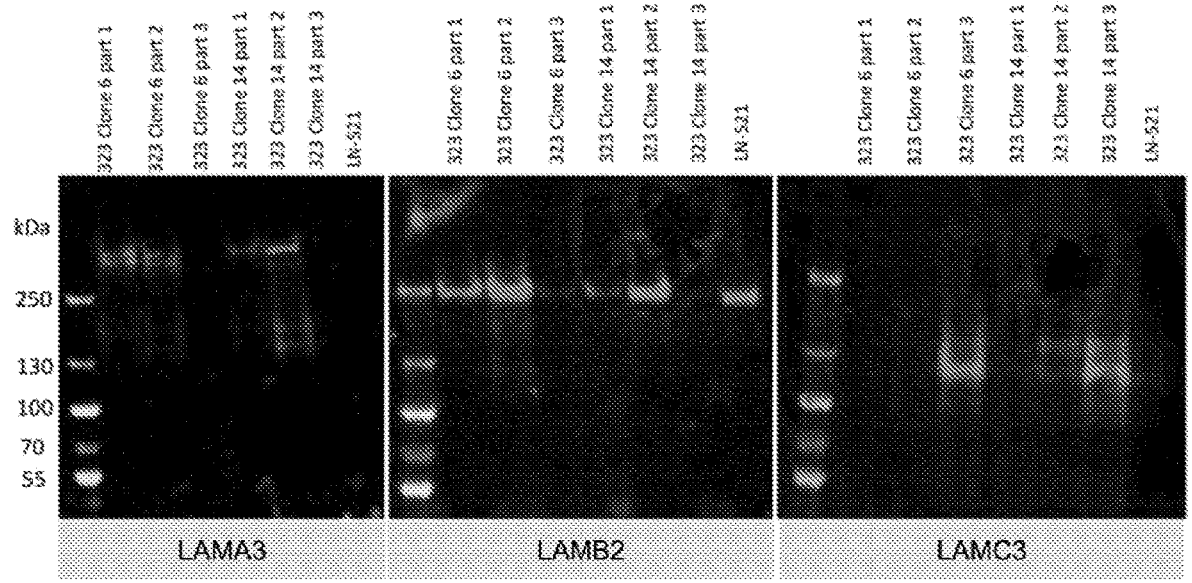
FIG. 1E is a Western blot showing the presence of LAMA3, LAMB2, and LAMC3 chains in the purified fractions or parts of LN-323.
Figure 1F:
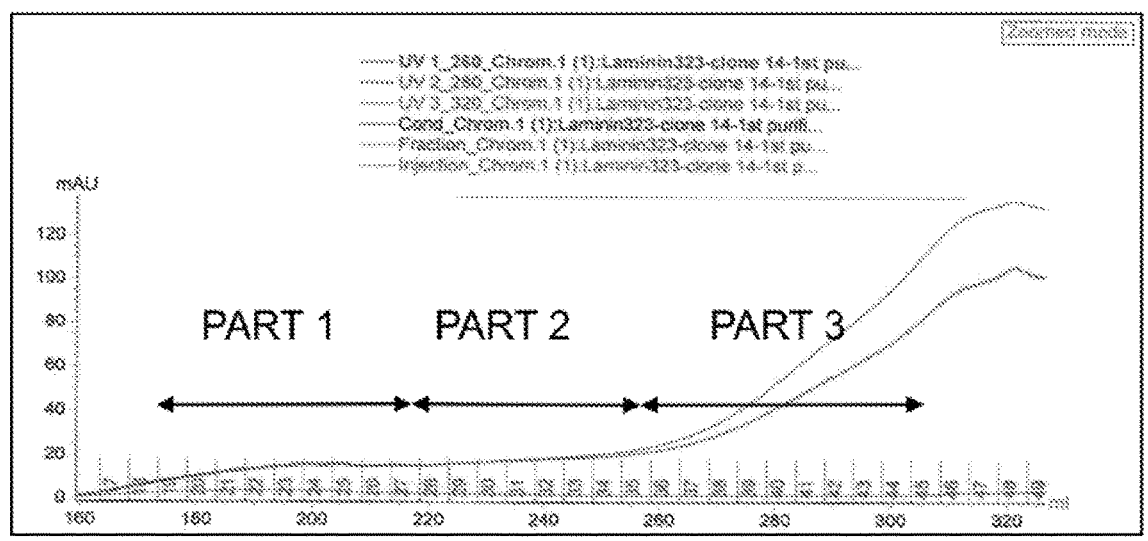
FIG. 1F is a chromatogram illustrating the protein elution profile of a LN-323 clone using the AKTA Chromatography System.

FIG. 1E is a Western blot showing the presence of laminin alpha-3, beta-2, and gamma-3 chains in the purified fractions or parts of LN-323. FIG. 1F is a chromatogram illustrating the protein elution profile of a LN-323 clone using the AKTA Chromatography System. FIG. 1G is LC-MS/MS (Liquid Chromatography-Mass Spectrophotometry) results showing that laminin alpha-3, beta-2, and gamma-3 chains are present.

Maintenance of hESCs

Culture plates (Costar) were coated with purified human LN isoform overnight at 4° C. at 10 µg/mL according to manufacturer's instructions (BioLamina). Pluripotent human embryonic stem cells (hESCs) were seeded and propagated in vitro on LN-521 where they maintained pluripotency. The hESC line H1 (WiCell Research Institute) was cultured in monolayer on LN pre-coated plates and maintained in NutriStem hESC XF (Biological Industries, Israel) medium. Upon confluency, the cells were sub-cultured by trypsinization using TrypLESelect (GIBCO Invitrogen) for 8 minutes at 37° C., 5% $CO_2$. The H1 cell line was routinely passaged at 10,000-20,000 cells/$cm^2$.

Photoreceptor Differentiation Protocol 24-well tissue culture plates (Costar) were coated with either (A) only LN-521; (B) a mixture of LN-523 and LN-521 (2:1 ratio); or (C) a mixture of LN-323+LN-521 (2:1 ratio). The plates were coated to obtain a final concentration of 10 µg/mL. The hESCs (H1) were plated at a seeding density of 70,000 cells/well and maintained in NutriStem with daily change of fresh medium for 2 days.

The basal medium used throughout the differentiation process consisted of GMEM (Glasgow Minimum Essential Medium, Life Technologies) supplemented with 0.1 mM of 3-mercaptoethanol (Life Technologies), 1× of non-essential amino acid solution (Gibco) and 1 mM of pyruvate (Gibco).

After reaching about 70% confluency for 2 days, the NutriStem was replaced with a neural induction media (NIM). NIM consists of 97% basal medium, 2% B27-without vitamin A (Life Technologies) supplement, 1% N2 supplement (CTS, Life Technologies), 5 µM SB431542 (Sigma) and 5 µM of CKI-7 (Sigma). NIM was changed once every 2 days from day 0 (D0) to D6.

On day 7 (D7) of differentiation, NIM was replaced by photoreceptor differentiation media (PRDM). PRDM consists of 97% basal medium, 2% B27—without vitamin A supplement, 1% N2 supplement (CTS), 10 ng/ml human BDNF (Brain-derived Neurotrophic Factor, PEPROTECH), 10 ng/ml human CNTF (Ciliary Neurotrophic Factor, PROSPEC-TANY TECHNOGENE), 0.5 µM retinoid acid (Tocris Bioscience), and 10 µM DAPT (N—[N-(3,5-Difluorophenacetyl-L-alanyl)]-S-phenylglycine t-Butyl Ester. Selleckchem). This medium was changed every other day until D30.

FIG. 2A is a diagram depicting the method of differentiating hESCs to photoreceptors. Three cell cultures are indicated: Nutristem for culturing prior to differentiation (Day 0); neural induction medium; and photoreceptor differentiation medium. Three pictures are also provided, showing the cells at D0, D20, and D30.

FIG. 2B and FIG. 2C are a set of five different graphs for the cells grown on the LN-523+LN-521 substrate. The top graph of FIG. 2B compares the expression of markers OCT3/4, NANOG, BRA, MIXL1, SOX17, FOXA2, and PAX6 between D0 cells and D20 cells. OCT3/4 and NANOG are upregulated on D0, while PAX6 is upregulated on D20.

The bottom left graph of FIG. 2B compares the expression of PAX6 for, going left to right, D0 LN-523+LN-521, D20 LN-523+LN-521, D20 LN-523 only, D30 LN-523+LN-521, and D30 LN-523 only. PAX6 is upregulated on D20 and D30 compared to D0.

The bottom right graph of FIG. 2B compares the expression of VSX2 (Visual System Homeobox 2) for, going left to right, D0 LN-523+LN-521, D20 LN-523+LN-521, D20 LN-523 only, D30 LN-523+LN-521, and D30 LN-523 only. VSX2 is upregulated on D20 and D30 compared to D0.

The left graph of FIG. 2C compares the expression of CRX (Cone Rod Homeobox protein) for, going left to right, D0 LN-523+LN-521, D20 LN-523+LN-521, D20 LN-523 only, D30 LN-523+LN-521, and D30 LN-523 only. CRX is upregulated on D20 and D30 compared to D0.

The right graph of FIG. 2C compares the expression of RCVRN (recoverin) for, going left to right, D0 LN-523+ LN-521, D20 LN-523+LN-521, D20 LN-523 only, D30 LN-523+LN-521, and D30 LN-523 only. RCVRN is upregulated on D30 compared to D0.

FIG. 2D and FIG. 2E are a set of five different graphs for the cells grown on the LN-323+LN-521 substrate. The top graph of FIG. 2D compares the expression of markers OCT3/4, NANOG, BRA, MIXL1, SOX17, FOXA2, and PAX6 between D0 cells and D20 cells. OCT3/4 and NANOG are upregulated on D0, while PAX6 is upregulated on D20.

The bottom left graph of FIG. 2D compares the expression of PAX6 for, going left to right, D0 LN-323+LN-521, D20 LN-323+LN-521, D20 LN-323 only, D30 LN323+LN-521, and D30 LN-323 only. PAX6 is upregulated on D20 and D30 compared to D0.

The bottom right graph of FIG. 2D compares the expression of VSX2 for, going left to right, D0 LN-323+LN-521, D20 LN-323+LN-521, D20 LN-323 only, D30 LN-323+ LN-521, and D30 LN323 only. VSX2 is upregulated on D20 and D30 compared to D0.

The left graph of FIG. 2E compares the expression of CRX for, going left to right, D0 LN-323+LN-521, D20 LN-323+LN-521, D20 LN-323 only, D30 LN-323+LN-521, and D30 LN-323 only. CRX is upregulated on D20 and D30 compared to D0.

The right graph of FIG. 2E compares the expression of RCVRN for, going left to right, D0 LN-323+LN-521, D20 LN-323+LN-521, D20 LN-323 only, D30 LN-323+LN-521, and D30 LN-323 only. RCVRN is upregulated on D20 and D30 compared to D0.

FIG. 2F and FIG. 2G are a set of five different graphs for the cells grown on a substrate of only LN-521. The top graph of FIG. 2F compares the expression of markers OCT3/4, NANOG, BRA, MIXL1, SOX17, FOXA2, and PAX6 between D0 cells and D20 cells. OCT3/4 and NANOG are upregulated on D0, while PAX6 is upregulated on D20.

The bottom left graph of FIG. 2F compares the expression of PAX6 for, going left to right, D0, D20, and D30. PAX6 is upregulated on D20 and D30 compared to D0.

The bottom right graph of FIG. 2F compares the expression of VSX2 for, going left to right, D0, D20, and D30. VSX2 is upregulated on D20 and D30 compared to D0.

The left graph of FIG. 2G compares the expression of CRX for, going left to right, D0, D20, and D30. CRX is upregulated on D20 and D30 compared to D0.

The bottom right graph of FIG. 2G compares the expression of RCVRN for, going left to right, D0, D20, and D30. RCVRN is upregulated on D20 and D30 compared to D0.

FIGS. 3A-3C are sets of pictures showing immunocytochemical analysis of D0 undifferentiated hESCs and D38 hESC-derived retinal cells. FIG. 3A is for cells grown on the LN-523+LN-521 substrate. FIG. 3B is for cells grown on the LN-523+LN-521 substrate. FIG. 3C is for cells grown on a substrate of only LN-521. Each set contains 10 micrographs, with scale bar=20 µm. In each set, the top row shows the analysis of D0 cells for OCT4, D0 cells for PAX6, and D38 cells for PAX6. The second row shows these merged with DAPI. The third row shows analysis of D38 cells for VSX2 and D38 cells for RCVRN. The fourth row shows these merged with DAPI. In D0 undifferentiated stem cells, OCT4 is expressed, but PAX6 (Paired box 6) is not. In the D38 differentiated cells, the markers PAX6, VSX2, and RCVRN are expressed.

FIG. 3D compares the expression of the markers PAX6, VSX2, CRX, and RCVRN across the three laminin matrices. From left to right, the matrices are LN-523:LN-521, LN-323:LN-521, and LN-521 only.

Example 2

Two independent single-cell RNA-sequencing datasets were generated with retinal progenitor cells derived from H1 embryonic stem cells at Day 20 and Day 30. H1 cells were cultured for 20 days and 30 days with the laminin protocol of Example 1. In each, RNA was isolated using a 10× genomics kit and sequenced using the Illumina Hi-Seq3000 sequencing platform. Reads were mapped to the human genome (Ensembl version 90) and quantified using Cell Ranger 2.1.1 10× Genomics software. The Cell Ranger software was provided with a custom built reference transcriptome generated by filtering the Ensembl transcriptome for the gene biotypes: protein coding, lincRNA and antisense. Cell Ranger was run with the expect number of cells parameter (expect-cells) set to 3000.

The Cell Ranger estimated number of cells was 1,790 and 3,881, Day 20 and Day 30 respectively. The total number of reads was 631,803,330 and 687,721,993, Day 20 and Day 30 respectively. The percentage of reads mapped to the human genome was 97.1% and 96.8%, Day 20 and Day 30 respectively. Cell Ranger returns the number of unique molecular identifiers (UMIs) associated with each gene (i.e. gene counts) and cell. Cell Ranger output matrices (i.e. genes.tsv and barcodes.tsv) were then input into R and genes with zero counts in all cells were discarded.

For each sample (i.e. Day 20 and Day 30 retinal progenitor cells), an independent analysis was carried out. In each analysis, cell quality control was performed by removing: (a) cells with very low and very high library size (i.e. cells below and above the $5^{th}$ and $99^{th}$ percentiles of the total cell library size respectively); (b) cells with low number of detected genes (i.e. cells below the $5^{th}$ percentile of the distribution formed by the total number of genes detected in each cell); and (c) cells with more than 10% of their total gene count coming from mitochondrial genes. After removing the cells that did not pass the cell quality control steps, gene count-per-million (CPM) were computed for all genes. Gene CPM was computed by providing the raw gene counts matrix to the function calculateCPM from scater 1.8.4 R package (McCarthy et al., 2017, Scater: pre-processing, quality control, normalization and visualization of single-cell RNA-seq data in R. Bioinformatics btw777). The function calculateCPM was run with the use_size_factors parameter set to FALSE.

In addition, in each separate analysis the following five gene quality control steps were taken: (a) only "detectable" genes were kept, defined as genes detected with more than one transcript in at least 1% of the total cells; (b) genes with low average expression in the data (i.e. genes with an average raw gene count expression below 0.01, this cutoff was set based on the total distribution of average gene expression across all cells and all genes) were removed; (c) genes with a high dropout rate were removed using M3Drop 3.09 R package (Andrews, 2017, M3Drop: Michaelis-Menten Modelling of Dropouts in single-cell RNASeq). In this step, the M3Drop false discovery rate (FDR) was used to rank all genes from low to high FDR and then the bottom 25% of genes (i.e. genes with highest dropout) were removed; (d) outlier genes in the gene expression distribution (i.e. "MALAT1" gene) were removed; and (e) genes encoded on the mitochondrial genome were removed.

After the gene quality control steps, gene counts were normalized with scran 1.8.4 R package (Lun et al., 2016, A step-by-step workflow for low-level analysis of single-cell RNA-seq data with Bioconductor. F1000Research 5, 2122). Scran size factors were computed from cell pools by doing a pre-clustering of the data with the quickCluster function. The output object of this function was provided to the computeSumFactors function and then Log2-transformed normalized counts were computed using the function normalize from the scater 1.8.4 R package (with default parameterizations) (McCarthy et al., 2017, Scater: pre-processing, quality control, normalization and visualization of single-cell RNA-seq data in R. Bioinformatics btw777). Then, to account for cell cycle effects, a G2M and G1 cell cycle phase score was computed for each cell by using cyclone function from the scater 1.8.4 R package (McCarthy et al., 2017). This function was supplied with the set of human cell cycle genes provided in (Scialdone et al., 2015, Computational assignment of cell-cycle stage from single-cell transcriptome data. Methods 85, 54-61). Afterwards, the $Log_2$-scran normalized genes counts were corrected for cell cycle effects by providing the counts and covariates "cell cycle G2M score" and "cell cycle G1 score" to the function removeBatchEffect from limma 3.36.3 R package (Ritchie et al., 2015, limma powers differential expression analyses for RNA-sequencing and microarray studies. Nucleic Acids Res. 43, e47-e47).

To identify genes marking cell subpopulations within the heterogeneous set of retinal progenitor cells, cell clustering was carried out using the SC3 1.8 R package (Kiselev et al., 2017 SC3: consensus clustering of single-cell RNA-seq data. Nat. Methods 14, 483-486). Highly variable genes were identified by using trendVar and decomposeVar functions from the scran 1.8.4 R package (Lun et al., 2016). All genes were ranked by the resulting false discovery rate (FDR) value (from low to high) and the top 50% of genes (representing the genes with highest variability) were used for cell clustering with SC3. SC3 was run using $Log_2$-scran normalized genes counts after correcting for cell cycle effects and the computed set of high variable genes only. SC3 was run with automatic detection of the number of clusters (i.e. K parameter, which was obtained by running the SC3 R package function sc3_estimate_k). This resulted in 19 and 21 cell clusters identified in the Day 20 and Day 30 retinal progenitor cells respectively.

In Day 20 retinal progenitor cells, marker genes for cells expressing PAX6 gene were identified. In Day 30 retinal progenitor cells, marker genes were identified for different subpopulations of cells: (a) cells expressing PAX6; (b) cells expressing CRX; and (c) cells expressing VSX2.

To identify marker genes for these sets of cells, in each of the two sets of clusters previously computed (19 and 21 cell clusters for Day 20 and Day 30 respectively), the median expression level of the gene-of-interest (e.g. PAX6) was computed by using the $Log_2$-scran normalized genes counts after correcting for cell cycle effects. Then, to obtain a single gene-of-interest-positive cell cluster clusters of cells with a gene-of-interest median $Log_2$ expression level higher than 0.58 (this value corresponds to 0.5 in the unlogged gene counts) were merged together. Pairwise differential expression analysis was then carried out between all the remaining clusters and the gene-of-interest-positive cell cluster. This differential expression analysis was carried out with edgeR 3.22.3 R package (Robinson et al., 2010, edgeR: a Bioconductor package for differential expression analysis of digital gene expression data. Bioinformatics 26, 139-140). EdgeR was run with non-normalized (raw) gene counts, the size factors computed with the scran 1.8.4 R package function sizeFactors and the edgeR R package functions estimateDisp, glmQLFit and glmQLFTest. Only the genes and cells that passed all the quality control steps described above were used. To account for cell cycle effects, the "cell cycle G2M score" and "cell cycle G1 score" were included in the edgeR model as computed above. After carrying out differential expression, cell cluster marker genes were defined as those genes that met two conditions: (a) a pairwise $Log_2$ fold change value higher than 2 when comparing with all the other clusters, and (b) $Log_2$ median expression level higher than 1 in the cluster in which the gene is declared a marker. This expression value corresponds to 1 in the unlogged gene counts.

In Day 30 retinal progenitor cells, gene markers were also computed for two more cell clusters: (a) the cell cluster number 1 obtained when running the SC3 algorithm with a K parameter of 2, denoted as the STMN2+ cluster; (b) the cell cluster number 3 obtained when running the SC3 algorithm with a K parameter of 3, denoted as the CNTN2+ cluster. Gene markers were computed for these cell clusters by running differential expression analysis and the steps described above.

Top genes marking each of these subpopulation of cells (i.e. Day 20 PAX6+ cells and Day 30 PAX6+ cells, VSX2+ cells, CRX+ cells, STMN2+ cells and CNTN2+ cells) were selected and their gene-gene pairwise Pearson correlation level was plotted in a histogram by using the function heatmap.2 from R package gplots 3.0.1 without scaling and default parameterizations (Warnes et al., 2016, gplots: Various R Programming Tools for Plotting Data) to obtain FIG. 5 and FIG. 6.

Day 20 and Day 30 progenitor cells were visualized separately by using t-distributed Stochastic Neighbor Embedding algorithm, t-SNE (McCarthy et al., 2017). t-SNE was computed with two dimensions and by providing the $Log_e$ scran-normalized and cell cycle adjusted gene counts to the function plotTSNE from scater 1.8.4 R package (McCarthy et al., 2017). The t-SNE perplexity parameter was set to the number of cells that passed quality control divided by 5. In the t-SNE graphs, each dot corresponds to an individual cell, and cell subpopulations were also visualized in these graphs by mapping each cell to the expression level of genes marking each of the subpopulations of Day 20 and Day 30 retinal progenitor cells (FIGS. 4C-4D, 7A-7J). Minimum and maximum colour was set to the minimum and maximum expression level of each of the genes plotted. A t-SNE graph was also generated for day 20 retinal progenitor cells coloured by the expression level of the genes NANOG and POU5F1 (FIGS. 4A-4B).

Day 20 retinal progenitor cells were found to lack expression of the genes NANOG and POU5F1 (FIG. 4A-4B). Day 20 retinal progenitor cells were also found to express PAX6 in a specific subpopulation of cells (FIG. 4C).

The following gene markers for Day 20 retinal progenitor cells that belong to this subpopulation of Day 20 cells expressing PAX6 were also identified (FIG. 5): DAPL1, SIX6 SFRP2, LHX2, PAX6, CDH2, CLDN1, TRPM3, RELN, DCT, and PMEL.

In Day 30 retinal progenitor cells, five distinct subpopulations of cells were identified (FIG. 6). These cell subpopulations were marked by the expression of the following genes:
  (a) CRX, C11orf96, NXPH4, NTS, DCT, PRDM1, NEUROD4, S100A13, RCVRN, FAM57B, SYT4, DLL3, SSTR2, CHRNA5 and ROBO2, (CRX+ subpopulation, including the cells highlighted in FIG. 7A and FIG. 7B);

(b) STMN2, ONECUT2, ATOH7, ELAVL4 and GAP43, (STMN2+ subpopulation, including the cells highlighted in FIG. 7C and FIG. 7D);

(c) CNTN2, NEFM, NEFL, PRPH, POU4F2 and CXCR4, (CNTN2+ subpopulation, including the cells highlighted FIG. 7E and FIG. 7F);

(d) PAX6, SIX3 and SLC2A1 (PAX6+ subpopulation, including the cells highlighted in FIG. 7G and FIG. 7H); and (e) VSX2, PTH2, FZD5, RARRES2, DIO3, SOX2 and CYP1B1 (VSX2+ subpopulation, including the cells highlighted in FIG. 7I and FIG. 7J).

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method for producing a population of photoreceptor progenitors or photoreceptors, comprising:
   plating pluripotent human stem cells on a cell culture surface having a laminin matrix thereon, wherein the laminin matrix comprises (i) a first laminin which is either laminin-323 or laminin-523, and (ii) a second laminin which is laminin-521, wherein the first laminin and the laminin-521 are each either an intact protein or a protein fragment; and
   culturing the pluripotent human stem cells to obtain photoreceptor progenitors or photoreceptors that express RCVRN.

2. The method of claim 1, wherein the pluripotent human stem cells are cultured by:
   culturing the cells in a neural induction medium comprising a TGFβ inhibitor and a Wnt inhibitor for a first time period; and
   culturing the cells in a photoreceptor differentiation medium comprising a brain derived neurotrophic factor (BDNF), a ciliary neutrotrophic factor (CNTF), retinoic acid, and a gamma secretase inhibitor for a second time period.

3. The method of claim 2, wherein the first time period is from about 120 hours to about 168 hours.

4. The method of claim 2, wherein the second time period is from about 288 hours to about 816 hours.

5. The method of claim 2, wherein the neural induction medium comprises:
   from about 5 µM to about 15 µM of the TGFβ inhibitor; and
   from about 5 µM to about 15 µM of the Wnt inhibitor.

6. The method of claim 2, wherein:
   the TGFβ inhibitor is SB431542; or
   the Wnt inhibitor is CKI-7.

7. The method of claim 2, wherein the photoreceptor differentiation medium comprises:
   from about 1 ng/ml to about 20 ng/ml of the brain derived neurotrophic factor (BDNF);
   from about 1 ng/ml to about 30 ng/ml of the ciliary neutrotrophic factor (CNTF);
   from about 0.1 µM to about 5 µM of retinoic acid; and
   from about 5 µM to about 15 µM of the gamma secretase inhibitor.

8. The method of claim 2, wherein the gamma secretase inhibitor is DAPT.

9. The method of claim 1, wherein the weight ratio of the first laminin to the second laminin is from about 1:1 to about 4:1.

10. The method of claim 1, wherein a population of photoreceptor progenitors is produced.

11. The method of claim 1, wherein a population of photoreceptors is produced.

12. The method of claim 1, wherein the first laminin is laminin-323.

13. The method of claim 1, wherein the first laminin is laminin-523.

14. The method of claim 1, wherein the first laminin and the laminin-521 are each an intact protein.

15. The method of claim 1, wherein the photoreceptor progenitors or photoreceptors express RCVRN and CRX.

* * * * *